(12) United States Patent
Furusako et al.

(10) Patent No.: US 11,472,892 B2
(45) Date of Patent: Oct. 18, 2022

(54) REACTIVE ALGINIC ACID DERIVATIVES

(71) Applicant: MOCHIDA PHARMACEUTICAL CO., LTD., Tokyo (JP)

(72) Inventors: Shoji Furusako, Tokyo (JP); Tsutomu Satoh, Tokyo (JP); Tomohiro Narumi, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 17/041,036

(22) PCT Filed: Mar. 27, 2019

(86) PCT No.: PCT/JP2019/013130
§ 371 (c)(1),
(2) Date: Sep. 24, 2020

(87) PCT Pub. No.: WO2019/189330
PCT Pub. Date: Oct. 3, 2019

(65) Prior Publication Data
US 2021/0024659 A1   Jan. 28, 2021

(30) Foreign Application Priority Data

Mar. 28, 2018  (JP) .............................. JP2018-062201

(51) Int. Cl.
*C08B 37/00* (2006.01)
(52) U.S. Cl.
CPC .................................. *C08B 37/0084* (2013.01)
(58) Field of Classification Search
None
See application file for complete search history.

(56) References Cited

U.S. PATENT DOCUMENTS

2010/0152423 A1   6/2010  Song
2016/0114046 A1   4/2016  Brudno et al.

FOREIGN PATENT DOCUMENTS

| FR | 2 967 678 A1 | 5/2012 |
|---|---|---|
| JP | 2003-516519 A | 5/2003 |
| JP | 2007-99902 A | 4/2007 |
| JP | 2010-512433 A | 4/2010 |
| JP | 2010-209130 A | 9/2010 |
| JP | 2015-502957 A | 1/2015 |
| JP | 2017-81904 A | 5/2017 |
| WO | WO 00/65352 A1 | 11/2000 |
| WO | WO 2004/099259 A1 | 11/2004 |
| WO | WO 2006/003014 A2 | 1/2006 |
| WO | WO 2013/086015 A1 | 6/2013 |
| WO | WO 2014/058359 A1 | 4/2014 |
| WO | WO 2015/154082 A1 | 10/2015 |
| WO | WO 2017/031167 A1 | 2/2017 |
| WO | WO 2017/031171 A1 | 2/2017 |

OTHER PUBLICATIONS

Xu, Journal of Biomaterials Applications 2016, 31(5), pp. 721-729. (Year: 2016).*
Brudno et al., "Refilling drug delivery depots through the blood", Proceedings of the National Academy of Sciences of the United States of America, Sep. 2, 2014, vol. 111, No. 35, pp. 12722-12727, Supporting Information pp. 1-6 and Supplemental Information.
International Search Report, issued in PCT/JP2019/013130, dated Jul. 2, 2019.
Khetan et al., "Degradation-mediated cellular traction directs stem cell fate in covalently crosslinked three-dimensional hydrogels", Nature Materials, May 2013, vol. 12, pp. 458-465.
Li et al., "Perfusion culture enhanced human endometrial stromal cell growth in alginate-multivalent integrin α5β1 ligand scaffolds", Journal of Biomedical Materials Research, Part A, Nov. 2011, vol. 99A, Issue 2, pp. 211-220.
Shtenberg et al., "Alginate modified with maleimide-terminated PEG as drug carriers with enhanced mucoadhesion", Carbohydrate Polymers, 2017, vol. 175, pp. 337-346.
Written Opinion of the International Searching Authority, issued in PCT/JP2019/013130, dated Jul. 2, 2019.
Xiao et al., "Nanoparticles With Surface Antibody Against CD98 and Carrying CD98 Small Interfering RNA Reduce Colitis in Mice", Gastroenterology, 2014, vol. 146, No. 5, pp. 1289-1300, e1-e19.
Extended European Search Report for corresponding European Application Nn. 19776505.0, dated Nov. 26, 2021.
Chinese Office Action and Search Report for Chinese Application No. 201980021846.4 dated Oct. 28, 2021, with English translation.
U.S. Appl. No. 17/763,071, filed Mar. 23, 2022, Not Yet Assigned.

* cited by examiner

*Primary Examiner* — Layla D Berry
(74) *Attorney, Agent, or Firm* — Birch, Stewart, Kolasch & Birch, LLP

(57) ABSTRACT

The present invention provides alginic acid derivatives having a group represented by general formula (I) or general formula (II) (the right side of the dashed line is excluded in each formula) at a portion of the carboxyl groups in an alginic acid. Novel alginic acid derivatives are thereby provided.

[C110]

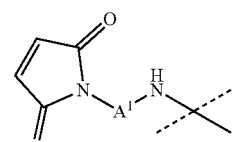

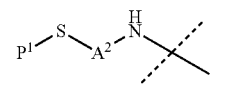

20 Claims, 3 Drawing Sheets

[Fig. 1]
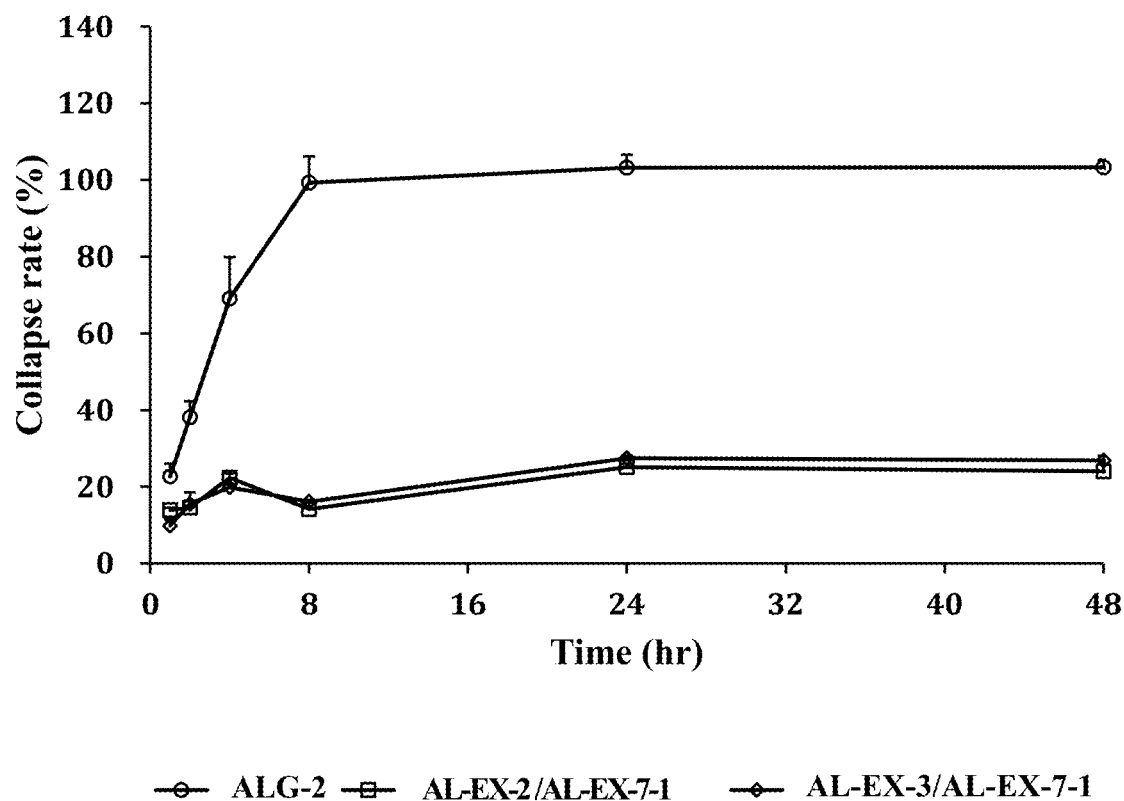

[Fig. 2]
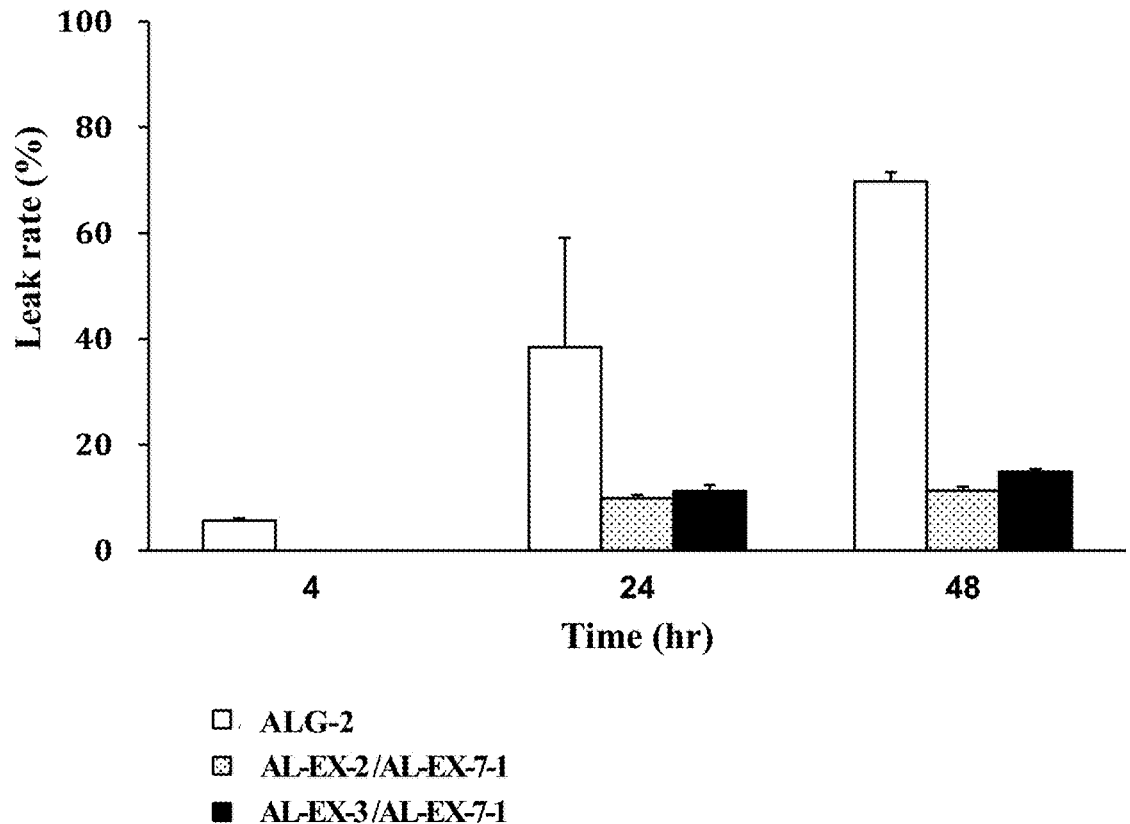
[Fig. 3]
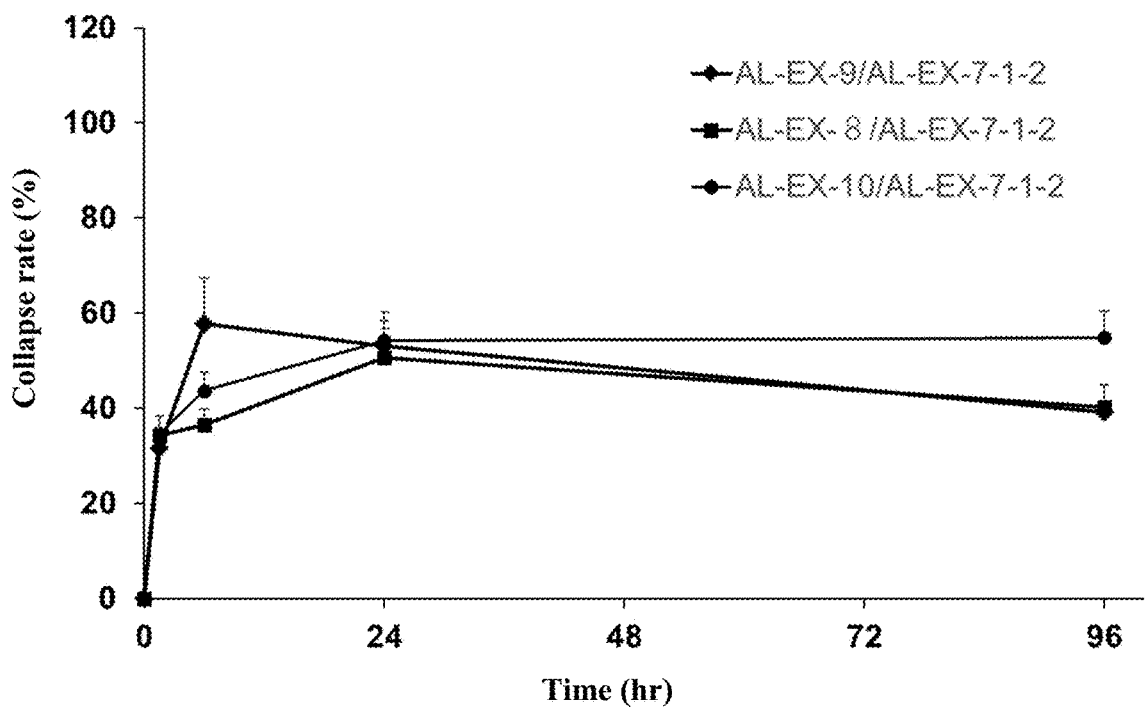

[Fig. 4]
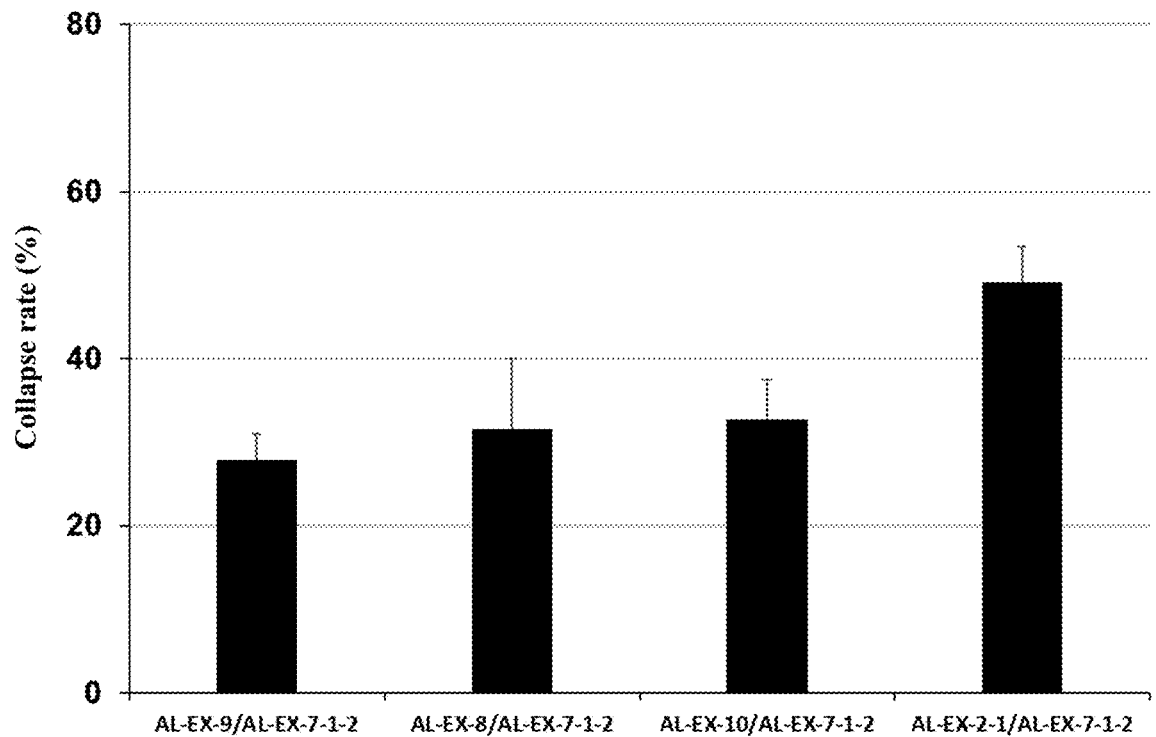
[Fig. 5]
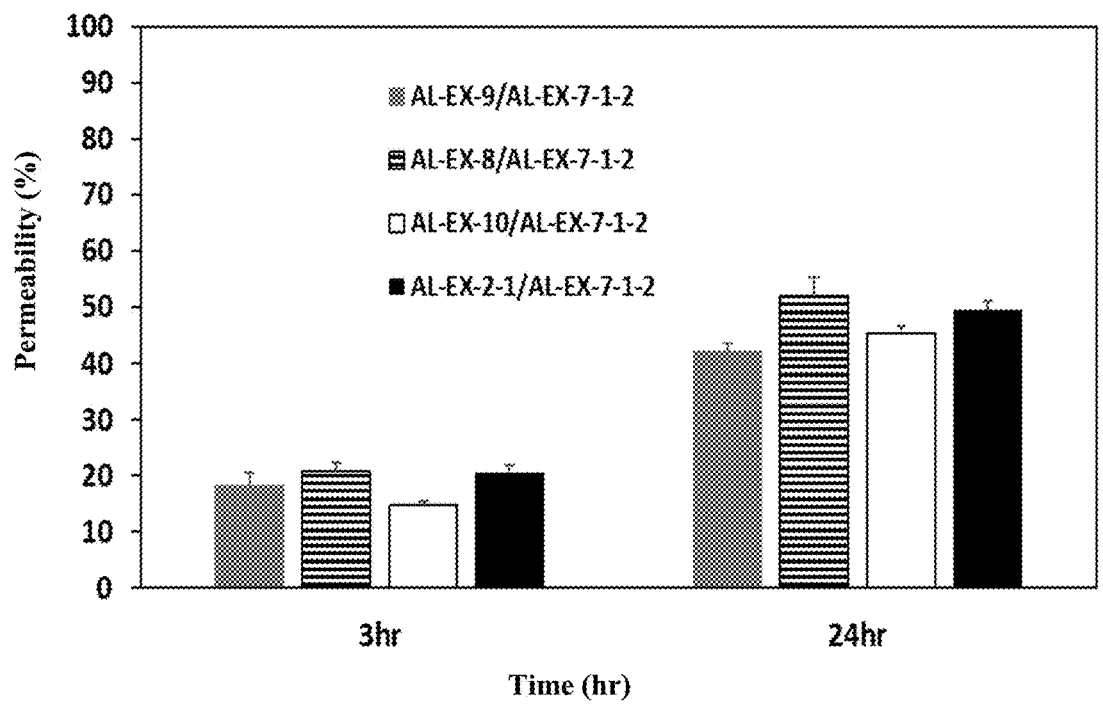

REACTIVE ALGINIC ACID DERIVATIVES

TECHNICAL FIELD

The present invention relates to alginic acid derivatives.

BACKGROUND ART

Alginic acid is a bioabsorbable polysaccharide that is extracted from brown algae such as *Lessonia, Macrocystis, Laminaria, Ascophyllum, Durvillea, Ecklonia cava, Eisenia bicyclis* and *Saccharina japonica*, and is a polymer obtained by linear polymerization of two kinds of uronic acid, D-mannuronic acid (M) and L-guluronic acid (G). More specifically, this is a block copolymer including a homopolymer fraction of D-mannuronic acid (UM fraction), a homopolymer fraction of L-guluronic acid (GG fraction), and a fraction of randomly arranged D-mannuronic acid and L-guluronic acid (M/G fraction) in arbitrary combination.

This kind of alginic acid is used in a wide range of fields such as foodstuffs, medicine, cosmetics, fibers, paper and the like.

Efforts have been made to modify alginic acid to make it more suitable for various purposes (Patent Literature 1 to 3). Maleimide and/or thiol have also been described as crosslinking groups for polysaccharide derivatives (Patent Literature 4 to 7).

CITATION LIST

Patent Literature

[Patent Literature 1] JP 2010-209130A
[Patent Literature 2] JP 2007-99902A
[Patent Literature 3] WO 2004/099259A1
[Patent Literature 4] JP 2003-516519A
[Patent Literature 5] JP 2015-502957A
[Patent Literature 6] FR 2967678A1
[Patent Literature 7] WO 2014/058359A1

SUMMARY OF INVENTION

Technical Problem

Under these circumstances, there is demand for novel alginic acid derivatives.

Solution to Problem

The inventors have completed the present invention as a result at earnest research aimed at solving these problems upon discovering that a specific alginic acid derivative having a specific introduced crosslinking group has improved stability after crosslinking.

That is, the present invention is described as Embodiments [1-1] to [22b] below.

[1-1] An alginic acid derivative including a group represented by formula (I) below (excluding part to the right of the broken line in the formula) at some of the carboxyl groups of at least one selected from the group consisting of alginic acid, esters thereof, and salts thereof:

[C1]

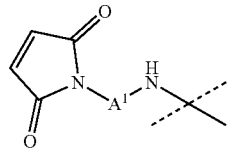

(I)

(wherein -A¹- is a linker selected from the group consisting of the following formulae (excluding parts outside the broken lines at both ends of each formula):

[C2]

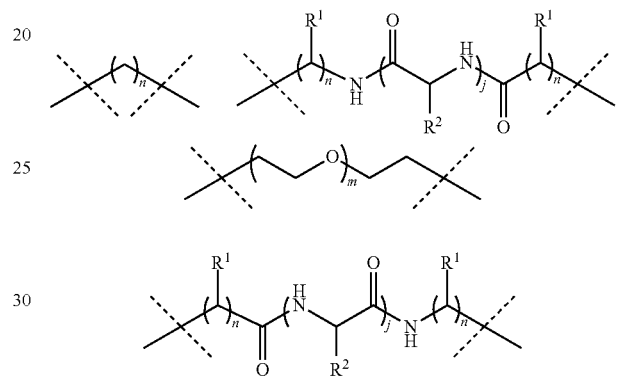

in which each $R^1$ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group and 4-imidazoylmethyl group and a propane-1,3-diyl group that forms a ring together with a carbon atom to which the $R^1$ binds and a nitrogen atom to which that carbon atom binds; each $R^1$ is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group and 4-imidazoylmethyl group and a propane-1,3-diyl group that forms a ring together with a carbon atom to which the $R^1$ binds and a nitrogen atom to which that carbon atom binds;

n is an integer from 1 to 18;
m is an integer from 1 to 9; and
j is an integer from 0 to 9).

[1-2] The alginic acid derivative according to [1-1] above, wherein -A¹- in formula (I) is a linker selected from the group consisting of the following formulae (excluding parts outside the broken lines at both ends of each formula):

[C3]

n is an integer from 1 to 18; and
m is an integer from 1 to 9.

[2] The alginic acid derivative according to [1-1] or [1-2] above, wherein -A$^1$- in formula (I) is a linker selected from the group consisting of the following formulae (excluding parts outside the broken lines at both ends of each formula):

[C4]

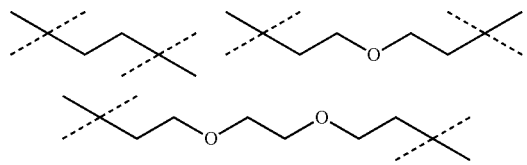

[3] An alginic acid derivative according to any one of [1-1] to [2] above, wherein the group represented by formula (I) is selected from the group consisting of the following formulae (excluding part to the right of the broken light in each formula):

[C5]

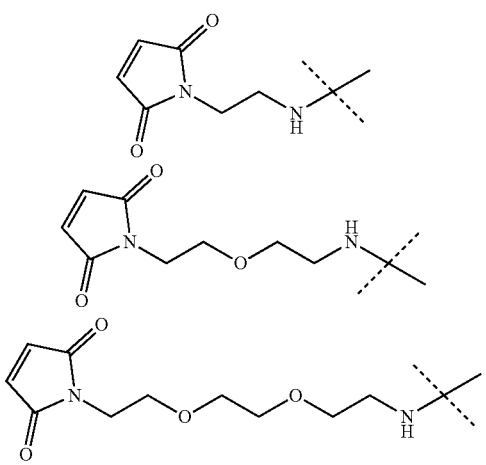

[4] The alginic acid derivative according to any one of [1-1] to [3] above, wherein the introduction rate of the crosslinking group is 1% to 30%.

[5] The alginic acid derivative according to any one of [1-1] to [4] above, wherein the weight-average molecular weight as measured by gel filtration chromatography of the alginic acid derivative is 100,000 Da to 3,000,000 Da.

[1a-1] An alginic acid derivative including a group represented by formula (I) below (excluding part to the right of the broken line in the formula) at some of the carboxyl groups of at least one selected from the group consisting of alginic acid, esters thereof, and salts thereof:

[C6]

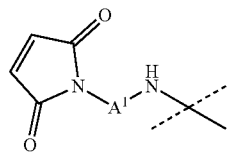

(I)

(wherein -A$^1$- is a linker selected from the group consisting of the following formulae (excluding parts outside the broken lines at both ends of each formula):

[C7]

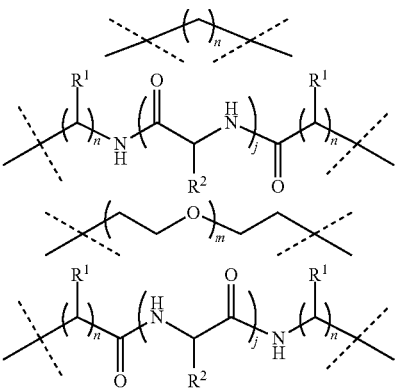

in which each R$^1$ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group and 4-imidazoylmethyl group and a propane-1,3-diyl group that forms a ring together with a carbon atom to which the R$^1$ binds and a nitrogen atom to which that carbon atom binds;

each R$^2$ is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group and 4-imidazoylmethyl group and a propane-1,3-diyl group that forms a ring together with a carbon atom to which the R$^2$ binds and a nitrogen atom to which that carbon atom binds;

n is an integer from 1 to 18;

m is an integer from 1 to 9; and j is an integer from 0 to 9).

[1a-2] The alginic acid derivative according to [1a-1] above, wherein -A$^1$- in formula (I) is a linker selected from the group consisting of the following formulae (excluding the parts outside the broken lines at both ends of each formula):

[C8]

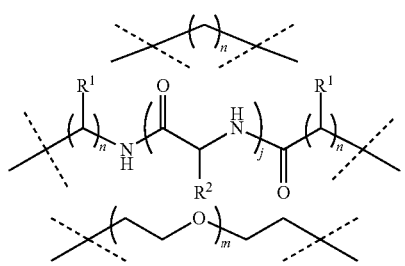

n is an integer from 1 to 18;
m is an integer from 1 to 9; and
j is an integer from 0 to 9.

[2a] The alginic acid derivative according to [1a-1] or [1a-2] above, wherein -A$^1$- in formula (I) is a linker selected from the group consisting of the following formulae (excluding the parts outside the broken lines at both ends of each formula):

[C9]

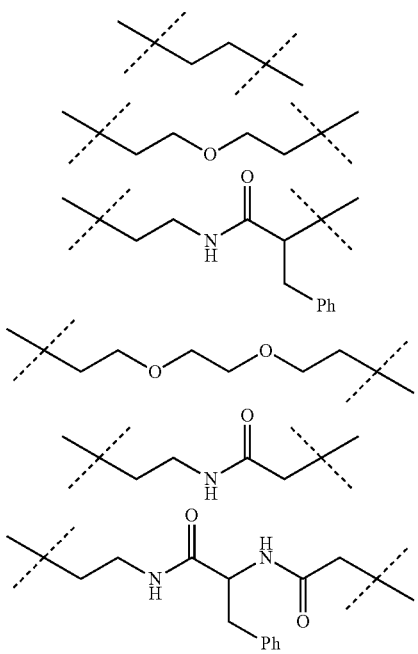

[2a-1] In Embodiment [2a] above, -A$^1$- is preferably a linker selected from the group consisting of the following formulae (excluding the parts outside the broken lines at both ends of each formula):

[C10]

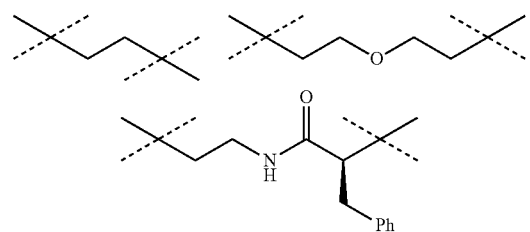

-continued

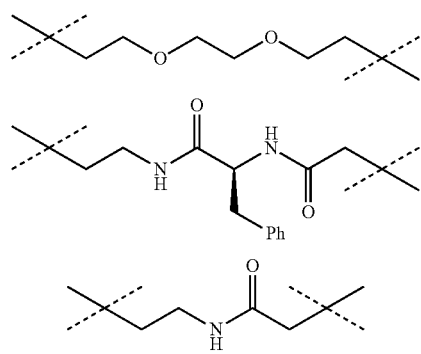

[3a] An alginic acid derivative according to any one of [1a-1] to [2a] above, wherein the group represented by formula (I) is selected from the group consisting of the following formulae (excluding the part to the right of the broken line in each formula):

[C11]

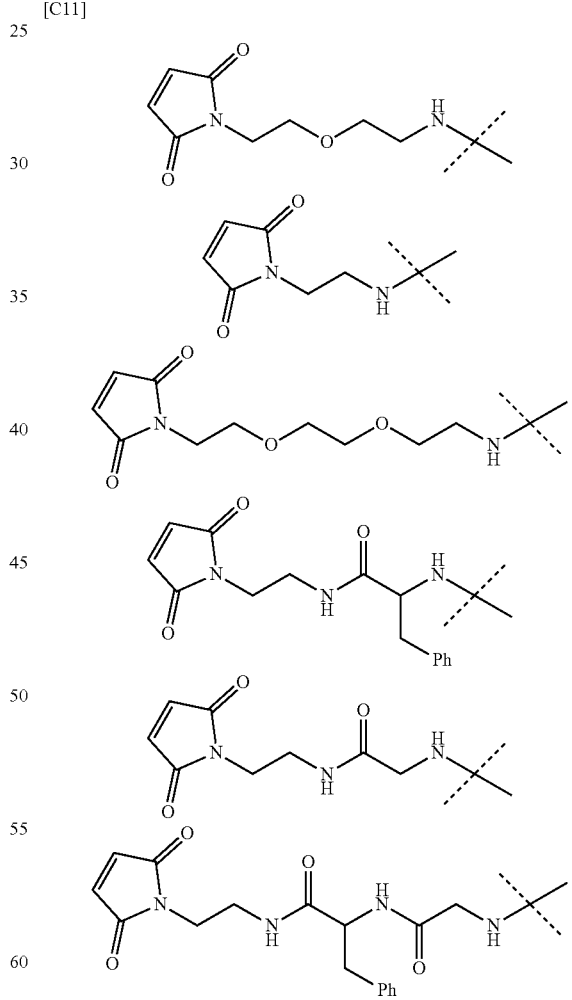

[3a-1] In Embodiment [3a] above, the group represented by formula (I) is preferably a group selected from the group consisting of the following formulae (excluding the part to the right of the broken line in each formula):

[C12]

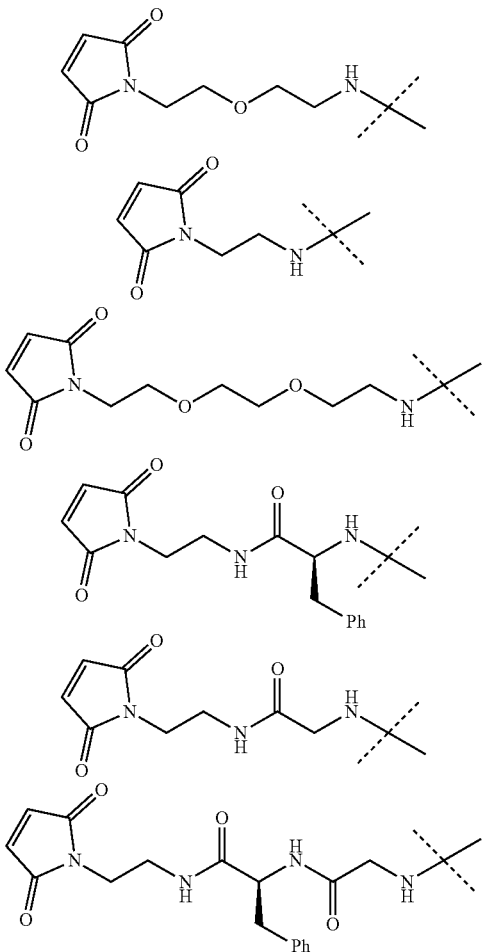

[4a] The alginic acid derivative according to any one of [1a-1] to [3a-1] above, wherein the introduction rate of the group represented by formula (I) is 1% to 30%. [5a] The alginic acid derivative according to any one of [1a-1] to [4a] above, wherein the weight-average molecular weight as measured by gel filtration chromatography of the alginic acid derivative is 100,000 Da to 3,000,000 Da.

[1b-1] An alginic acid derivative including a group represented by formula (I) below (excluding the part to the right of the broken line in the formula) at some of the carboxyl groups of at least one selected from the group consisting of alginic acid, esters thereof, and salts thereof:

[C13]

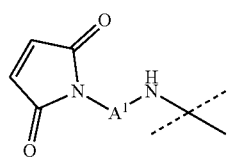

(I)

(wherein -A$^1$- is a linker selected from the group consisting of the following formulae (excluding the parts outside the broken lines at both ends of each formula):

[C14]

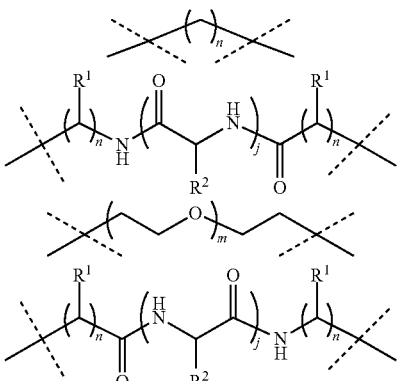

In which each R$^1$ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group and 4-imidazoylmethyl group and a propane-1, 3-diyl group that forms a ring together with a carbon atom to which the R$^1$ binds and a nitrogen atom to which that carbon atom binds;
each R$^2$ is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group and 4-imidazoylmethyl group and a propane-1,3-diyl group that forms a ring together with a carbon atom to which the R$^2$ binds and a nitrogen atom to which that carbon atom binds;
n is an integer from 1 to 18;
m is an integer from 1 to 9; and
j is an integer from 0 to 9)
(provided that —CH$_2$CH$_2$— as -A$^1$- is excluded).
[1b-2] The alginic acid derivative according to [1b-1] above, wherein -A$^1$- in formula (I) is a linker selected from the group consisting of the following formulae (excluding the parts outside the broken lines at both ends of each formula):

[C15]

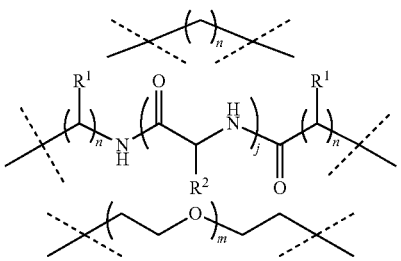

n is an integer from 1 to 18;
m is an integer from 1 to 9; and
j is an integer from 0 to 9
(provided that —CH$_2$CH$_2$— as -A$^1$- is excluded).

[2b] An alginic acid derivative according to [1b-1] or [1b-2] above, wherein -A¹- in formula (I) is a linker selected from the group consisting of the following formulae (excluding the parts outside the broken lines at both ends of each formula):

[C16]

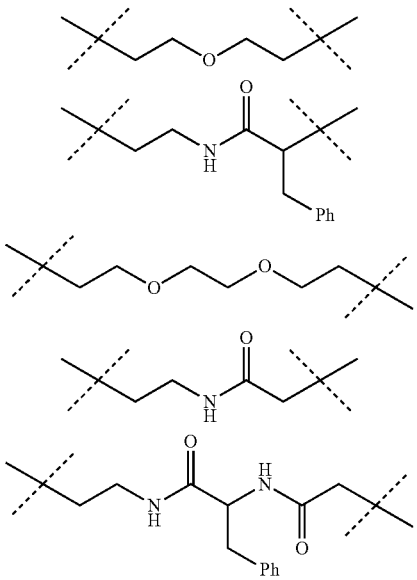

[2b-1] In Embodiment [2b] above, -A¹- is preferably a linker selected from the group consisting of the following formulae (excluding the parts outside the broken lines at both ends of each formula):

[C17]

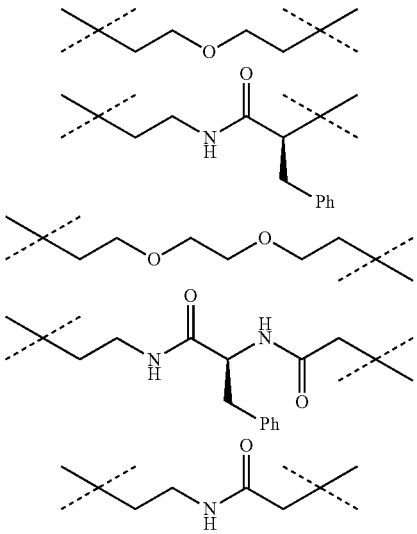

[3b] The alginic acid derivative according to any one of [1b-1] to [2b] above, wherein the group represented by formula (I) is selected from the group consisting of the following formulae (excluding the part to the right of the broken line in each formula):

[C18]

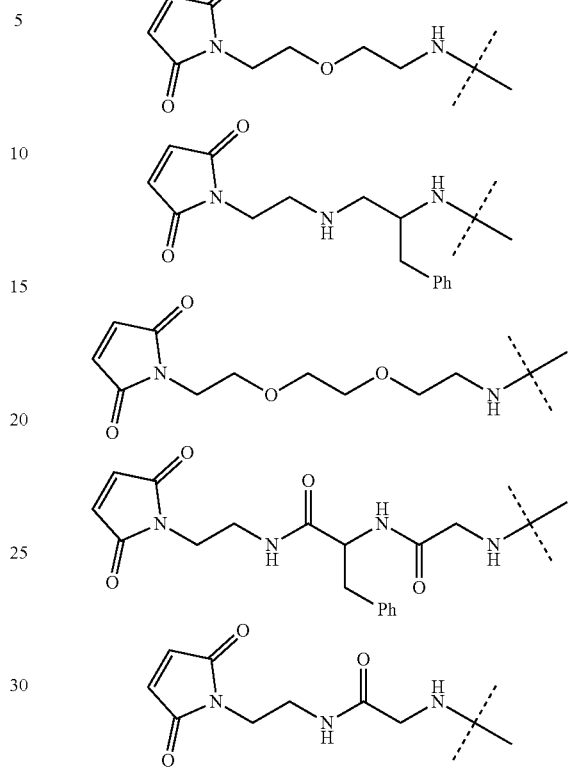

[3b-1] In Embodiment [3b] above, the group represented by formula (I) is preferably selected from the group consisting of the following formulae (excluding the part to the right of the broken line in each formula):

[C19]

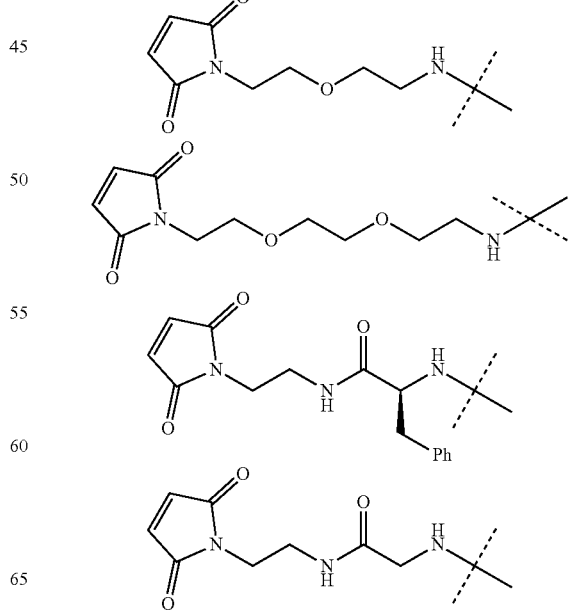

-continued

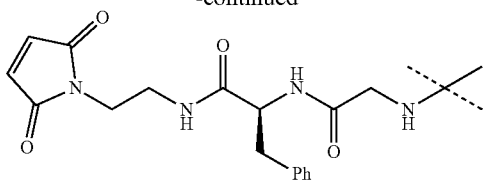

[4b] The alginic acid derivative according to any one of [1b-1] to [3b-1] above, wherein the introduction rate of the group represented by formula (I) is 1% to 30%.

[5b] The alginic acid derivative according to any one of [1b-1] to [4b] above, wherein the weight-average molecular weight as measured by gel filtration chromatography of the alginic acid derivative is 100,000 Da to 3,000,000 Da.

[6] An alginic acid derivative including a crosslinking group represented by formula (II) below (excluding the part to the right of the broken line in the formula) at some of the carboxyl groups of at least one selected from the group consisting of alginic acid, esters thereof, and salts thereof:

[C20]

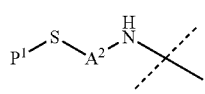

(II)

(wherein $P^1$ is a hydrogen atom or a protecting group of a thiol (—SH) group, and $-A^2-$ is a linker represented by the following formula (excluding the parts outside the broken lines at both ends of the formula):

[C21]

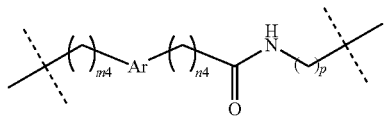

and in $-A^2-$ above, Ar is a phenylene group optionally substituted with (for example 1 or 2) water-soluble substituents;

n4 is an integer from 0 to 10;
m4 is an integer from 0 to 10; and
p is an integer from 0 to 10).

[7] The alginic acid derivative according to [6] above, wherein $P^1$ in formula (II) is a hydrogen atom, an acetyl group or a benzoyl group.

[7-1] The alginic acid derivative according to [6] above, wherein $P^1$ in formula (II) is a hydrogen atom or an acetyl group.

[8] The alginic acid derivative according to any one of [6] to [7-1] above, wherein Ar in $-A^2-$ in formula (II) is a p-phenylene group.

[8-1] The alginic acid derivative according to any one of [6] to [7-1] above, wherein $-A^2-$ is a linker selected from the group consisting of the following formulae (excluding the parts outside the broken lines at both ends of each formula):

[C22]

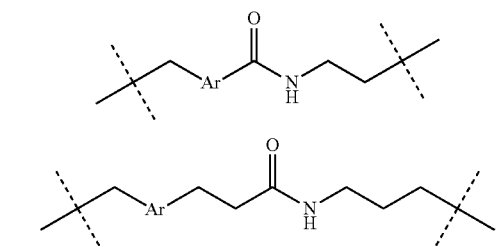

and Ar is a p-phenylene group.

[9] The alginic acid derivative according to any one of [6] to [8-1] above, wherein the group represented by formula (II) is selected from the group consisting of the following formulae (excluding the part to the right of the broken line in each formula):

[C23]

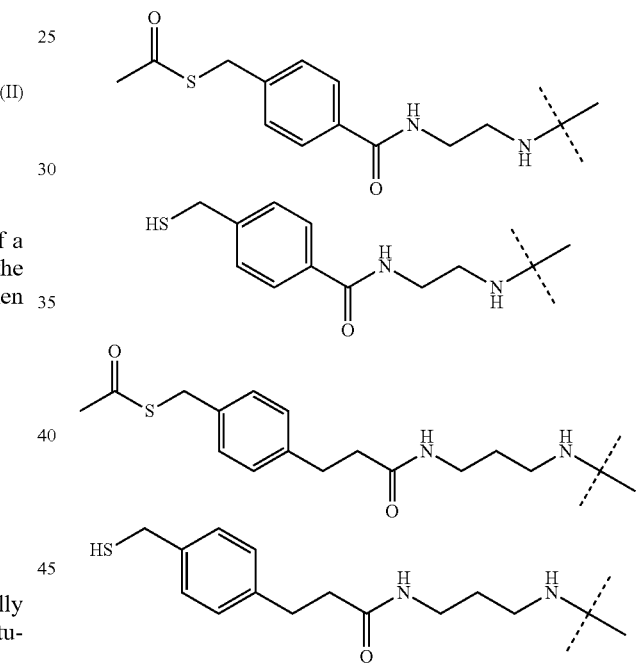

[9-1] The alginic acid derivative according to any one of [6] to [8-1] above, wherein the group represented by formula (II) is selected from the group consisting of the following formulae (excluding the part to the right of the broken line in each formula):

[C24]

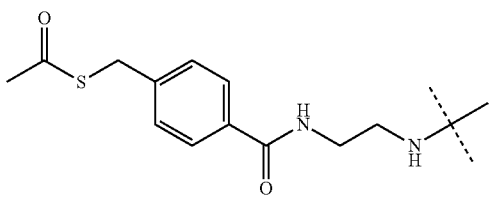

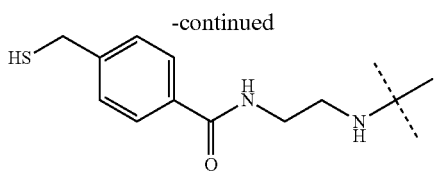

[10] The alginic acid derivative according to any one of [6] to [9-1] above, wherein the introduction rate of the group represented by formula (II) (also called the "crosslinking group introduction rate") is 1% to 30%.

[11] The alginic acid derivative according to any one of [6] to [10] above, wherein the weight-average molecular weight as measured by gel filtration chromatography of the alginic acid derivative is 100,000 Da to 3,000,000 Da.

[12] A composition containing an alginic acid derivative according to any one of [1-1] to [5] above and an alginic acid derivative according to any one of [6] to [11] above.

[12a] A composition containing an alginic acid derivative according to any one of [1a-1] to [5a] above and an alginic acid derivative according to any one of [6] to [11] above.

[12b] A composition containing an alginic acid derivative according to any one of [1b-1] to [5b] above and an alginic acid derivative according to any one of [6] to [11] above.

[13-1] A crosslinked alginic acid structure obtained by subjecting an alginic acid derivative according to any one of [1-1] to [5] above and an alginic acid derivative according to any one of [6] to [11] above to a crosslinking reaction.

[13a-1] A crosslinked alginic acid structure obtained by subjecting an alginic acid derivative according to any one of [1a-1] to [5a] above and an alginic acid derivative according to any one of [6] to [11] above to a crosslinking reaction.

[13b-1] A crosslinked alginic acid structure obtained by subjecting an alginic acid derivative according to any one of [1b-1] to [5b] above and an alginic acid derivative according to any one of [6] to [11] above to a crosslinking reaction.

[13-2] The crosslinked alginic acid structure according to [13-1] above, wherein the crosslinked alginic acid structure is obtained by dripping a solution of an alginic acid derivative according to any one of [1-1] to [5] above into a solution containing a calcium ion, and then subjecting the resulting gel to a crosslinking reaction in a solution of an alginic acid derivative according to any one of [6] to [11] above.

[13a-2] The crosslinked alginic acid structure according to [13a-1] above, wherein the crosslinked alginic acid structure is obtained by dripping a solution of an alginic acid derivative according to any one of [1a-1] to [5a] above into a solution containing a calcium ion, and then subjecting the resulting gel to a crosslinking reaction in a solution of an alginic acid derivative according to any one of [6] to [11] above.

[13b-2] The crosslinked alginic acid structure according to [13b-1] above, wherein the crosslinked alginic acid structure is obtained by dripping a solution of an alginic acid derivative according to any one of [1b-1] to [5b] above into a solution containing a calcium ion, and then subjecting the resulting gel to a crosslinking reaction in a solution of an alginic acid derivative according to any one of [6] to [11] above.

[13-3] The crosslinked alginic acid structure according to [13-1] above, wherein the crosslinked alginic acid structure is obtained by dripping a solution of an alginic acid derivative according to any one of [6] to [11] above into a solution containing a calcium ion, and then subjecting the resulting gel to a crosslinking reaction in a solution containing an alginic acid derivative according to any one of [1-1] to [5] above.

[13a-3] The crosslinked alginic acid structure according to [13a-1] above, wherein the crosslinked alginic acid structure is obtained by dripping a solution of an alginic acid derivative according to any one of [6] to [11] above into a solution containing a calcium ion, and then subjecting the resulting gel to a crosslinking reaction in a solution containing an alginic acid derivative according to any one of [1a-1] to [5a] above.

[13b-3] The crosslinked alginic acid structure according to [13b-1] above, wherein the crosslinked alginic acid structure is obtained by dripping a solution of an alginic acid derivative according to any one of [6] to [11] above into a solution containing a calcium ion, and then subjecting the resulting gel to a crosslinking reaction in a solution containing an alginic acid derivative according to any one of [1b-1] to [5b] above.

[13-4] The crosslinked alginic acid structure according to [13-1] above, wherein the crosslinked alginic acid structure is obtained by dripping a solution of the composition according to [12] above into a solution containing a calcium ion.

[13a-4] The crosslinked alginic acid structure according to [13a-1] above, wherein the crosslinked alginic acid structure is obtained by dripping a solution of the composition according to [12a] above into a solution containing a calcium ion.

[13b-4] The crosslinked alginic acid structure according to [13b-1] above, wherein the crosslinked alginic acid structure is obtained by dripping a solution of the composition according to [12b] above into a solution containing a calcium ion.

[13-5] The crosslinked alginic acid structure according to any one of [13-1] to [13-4] above, wherein the crosslinked alginic acid structure is a fiber, bead, nearly spherical gel or microcapsule.

[13a-5] The crosslinked alginic acid structure according to any one of [13a-1] to [13a-4] above, wherein the crosslinked alginic acid structure is a fiber, bead, nearly spherical gel or microcapsule.

[13b-5] The crosslinked alginic acid structure according to any one of [13b-1] to [13b-4] above, wherein the crosslinked alginic acid structure is a fiber, bead, nearly spherical gel or microcapsule.

[14] A medical material containing a crosslinked alginic acid structure according to any one of [13-1] to [13-5] above.

[14a] The medical material containing a crosslinked alginic acid structure according to any one of [13a-1] to [13a-5] above.

[14b] The medical material containing a crosslinked alginic acid structure according to any one of [13b-1] to [13b-5] above.

[15] The medical material according to [14] above, wherein the crosslinked alginic acid structure is a bead or a nearly spherical gel.

[15a] The medical material according to [14a] above, wherein the crosslinked alginic acid structure is a bead or a nearly spherical gel.

[15b] The medical material according to [14b] above, wherein the crosslinked alginic acid structure is a bead or a nearly spherical gel.

[16] A method for manufacturing a crosslinked alginic acid structure, including dripping a solution of an alginic acid derivative according to any one of [1-1] to [5] above into a solution containing a calcium ion, and then subjecting the resulting gel to a crosslinking reaction in a solution of an alginic acid derivative according to any one of [6] to [11] above.

[16a] A method for manufacturing a crosslinked alginic acid structure, including dripping a solution of an alginic acid derivative according to any one of [1a-1] to [5a] above into a solution containing a calcium ion, and then subjecting the resulting gel to a crosslinking reaction in a solution of an alginic acid derivative according to any one of [6] to [11] above.

[16b] A method for manufacturing a crosslinked alginic acid structure, including dripping a solution of an alginic acid derivative according to any one of [1b-1] to [5b] above into a solution containing a calcium ion, and then subjecting the resulting gel to a crosslinking reaction in a solution of an alginic acid derivative according to any one of [6] to [11] above.

[17] A method for manufacturing a crosslinked alginic acid structure, including dripping a solution of an alginic acid derivative according to any one of [6] to [11] above into a solution containing a calcium ion, and then subjecting the resulting gel to a crosslinking reaction in a solution containing an alginic acid derivative according to any one of [1-1] to [5] above.

[17a] A method for manufacturing a crosslinked alginic acid structure, including dripping a solution of an alginic acid derivative according to any one of [6] to [11] above into a solution containing a calcium ion, and then subjecting the resulting gel to a crosslinking reaction in a solution containing an alginic acid derivative according to any one of [1a-1] to [5a] above.

[17b] A method for manufacturing a crosslinked alginic acid structure, including dripping a solution of an alginic acid derivative according to any one of [6] to [11] above into a solution containing a calcium ion, and then subjecting the resulting gel to a crosslinking reaction in a solution containing an alginic acid derivative according to any one of [1b-1] to [5b] above.

[18] A method for manufacturing a crosslinked alginic acid structure, including dripping a solution of the composition according to [12] above into a solution containing a calcium ion.

[18a] A method for manufacturing a crosslinked alginic acid structure, including dripping a solution of the composition according to [12a] above into a solution containing a calcium ion.

[18b] A method for manufacturing a crosslinked alginic acid structure, including dripping a solution of the composition according to [12b] above into a solution containing a calcium ion.

[19] A method for manufacturing a crosslinked alginic acid structure, including partially crosslinking an alginic acid derivative according to any one of [1-1] to [5] above with a divalent metal ion to obtain a specific structure, and then subjecting this specific structure to a crosslinking reaction with an alginic acid derivative according to any one of [6] to [11] above.

[19a] A method for manufacturing a crosslinked alginic acid structure, including partially crosslinking an alginic acid derivative according to any one of [1a-1] to [5a] above with a divalent metal ion to obtain a specific structure, and then subjecting this specific structure to a crosslinking reaction with an alginic acid derivative according to any one of [6] to [11] above.

[19b] A method for manufacturing a crosslinked alginic acid structure, including partially crosslinking an alginic acid derivative according to any one of [1b-1] to [5b] above with a divalent metal ion to obtain a specific structure, and then subjecting this specific structure to a crosslinking reaction with an alginic acid derivative according to any one of [6] to [11] above.

[20] A method for manufacturing a crosslinked alginic acid structure, including partially crosslinking an alginic acid derivative according to any one of [6] to [11] above with a divalent metal ion to obtain a specific structure, and then subjecting this specific structure to a crosslinking reaction with an alginic acid derivative according to any one of [1-1] to [5] above.

[20a] A method for manufacturing a crosslinked alginic acid structure, including partially crosslinking an alginic acid derivative according to any one of [6] to [11] above with a divalent metal ion to obtain a specific structure, and then subjecting this specific structure to a crosslinking reaction with an alginic acid derivative according to any one of [1a-1] to [5a] above.

[20b] A method for manufacturing a crosslinked alginic acid structure, including partially crosslinking an alginic acid derivative according to any one of [6] to [11] above with a divalent metal ion to obtain a specific structure, and then subjecting this specific structure to a crosslinking reaction with an alginic acid derivative according to any one of [1b-1] to [5b] above.

[21] A method for manufacturing a crosslinked alginic acid structure, including partially crosslinking a composition according to [12] above with a divalent metal ion.

[21a] A method for manufacturing a crosslinked alginic acid structure, including partially crosslinking a composition according to [12a] above with a divalent metal ion.

[21b] A method for manufacturing a crosslinked alginic acid structure, including partially crosslinking a composition according to [12b] above with a divalent metal ion.

[22] A crosslinked alginic acid structure having the ability to retain contents, obtained by a crosslinking reaction that includes using an alginic acid derivative according to any one of [1-1] to [5] above, an alginic acid derivative according to any one of [6] to [11] above and a divalent metal ion.

[22a] A crosslinked alginic acid structure having the ability to retain contents, obtained by a crosslinking reaction that includes using an alginic acid derivative according to any one of [1a-1] to [5a] above, an alginic acid derivative according to any one of [6] to [11] above and a divalent metal ion.

[22b] A crosslinked alginic acid structure having the ability to retain contents, obtained by a crosslinking reaction that includes using an alginic acid derivative according to any one of [1b-1] to [5b] above, an alginic acid derivative according to any one of [6] to [11] above and a divalent metal ion.

Advantageous Effects of Invention

The present invention provides a novel alginic acid derivative. Preferably, the alginic acid derivative has improved stability after crosslinking.

BRIEF DESCRIPTION OF DRAWINGS

FIG. 1 is a graph showing an evaluation of the gel stability of crosslinked alginic acid structure (ALG-2, AL-EX-2/AL-EX-7-1 or AL-EX-3/AL-EX-7-1).

FIG. 2 is a graph showing an evaluation of the gel leak rates of crosslinked alginic acid structure (AL-2, AL-EX-2/AL-EX-7-1 or AL-EX-3/AL-EX-7-1).

FIG. 3 is a graph showing an evaluation of the gel stability of crosslinked alginic acid structure (AL-EX-8/AL-EX-7-1-2, AL-EX-9/AL-EX-7-1-2 or AL-EX-10/AL-EX-7-1-2).

FIG. 4 is a graph showing an evaluation of the gel stability of crosslinked alginic acid structure (AL-EX-8/AL-EX-7-1-2, AL-EX-9/AL-EX-7-1-2, AL-EX-10/AL-EX-7-1-2 or AL-EX-2-1/AL-EX-7-1-2) after EDTA treatment.

FIG. 5 is a graph showing an evaluation of the gel permeability of alginic acid structure (AL-EX-8/AL-EX-7-1-2, AL-EX-9/AL-EX-7-1-2, AL-EX-10/AL-EX-7-1-2 or AL-EX-2-1/AL-EX-7-1-2).

DESCRIPTION OF EMBODIMENTS

The present invention is explained in detail below.

1. Alginic Acid Derivative

An alginic acid derivative is provided here. In the alginic acid derivative, some of the carboxyl groups of alginic acid are substituted with a crosslinking group (also called a "reactive group") via a linker. That is, for example any one or more carboxyl groups of alginic acid may form an amide bond with a linker (-L-) having a crosslinking group (Z) and an amino group at either end (formula AL-1 below, in which Z is a crosslinking group and -L- is a linker; for example, -L- may be -A$^1$- in formula (I) above or -A$^2$- in formula (II) above).

[C25]

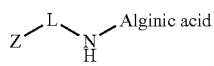
(AL-1)

The crosslinking group is an acrylic acid residue or thiol residue for example. As crosslinking groups, both acrylic acid residues and thiol residues easily form covalent bonds by a Michael addition reaction.

Examples of acrylic acid residues include residues capable of forming Michael adducts by reacting with thiol residues, and specific examples include acrylic acid, maleic acid, maleimide, fumaric acid and the like. Examples of thiol residues include residues capable of forming Michael adducts by reacting with acrylic acid residues, and specific examples include HS—$(CH_2)_{m4}$-Ph (m4=0 to 10, preferably m4=0 to 2). Preferred examples of thiol residues include benzylthiol, thiophenol and the like.

The crosslinking group may preferably be any that easily forms a Michael adduct by a Michael addition reaction, such as an acryloyl group as an acrylic acid residue or a thiol group as a thiol residue; a maleimide group is more preferred as an acrylic acid residue, and a benzylthiol group is more preferred as a thiol residue.

The crosslinking group may also have bound thereto a linker (spacer) that binds to both the crosslinking group and the alginic acid to maintain a certain distance between the two. Preferred is an alginic acid derivative having maleimide, benzylthiol or a protected thiol group of benzylthiol bound thereto as a crosslinking group via a linker.

The following alginic acid derivative is provided by some embodiments.

An alginic acid derivative including a crosslinking group (reactive group) represented by formula (I) below (excluding the part to the right of the broken line in the formula) at some of the carboxyl groups of at least one kind of alginate selected from the group consisting of alginic acid, esters thereof, and salts thereof:

[C26]

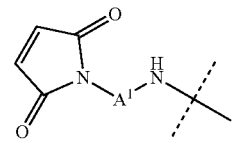
(I)

(wherein -A$^1$- is a linker selected from the group consisting of the following formulae (excluding the parts outside the broken lines at both ends of each formula):

[C27]

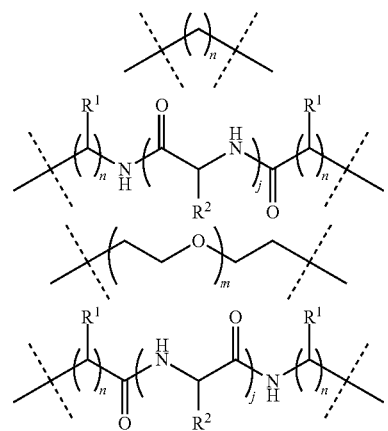

in which each R$^1$ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group and 4-imidazoylmethyl group and a propane-1,3-diyl group that forms a ring together with a carbon atom to which the R$^1$ binds and a nitrogen atom to which that carbon atom binds;

each R$^2$ is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group and 4-imidazoylmethyl group and a propane-1,3-diyl group that forms a ring together with a carbon atom to which the R$^2$ binds and a nitrogen atom to which that carbon atom binds;

n is an integer from 1 to 18;

m is an integer from 1 to 9; and j is an integer from 0 to 9).

-A$^1$-=—$CH_2CH_2$— is excluded from some embodiments of the alginic acid derivative.

The following alginic acid derivative is provided by some other embodiments.

An alginic acid derivative including a group represented by formula (II) below (excluding the part to the right of the broken line in the formula) at some of the carboxyl groups of at least one selected from the group consisting of alginic acid, esters thereof, and salts thereof:

[C28]

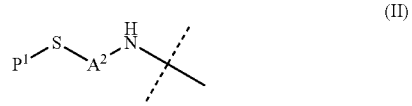
(II)

(wherein $P^1$ is a hydrogen atom or a protecting group of a thiol (—SH) group, and $-A^2-$ is a linker represented by the following formula (excluding the parts outside the broken lines at both ends of the formula):

[C29]

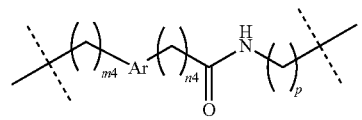

and in $-A^2-$ above, Ar is a phenylene group optionally substituted with (for example 1 to 3) water-soluble substituents;
n4 is an integer from 0 to 10;
m4 is an integer from 0 to 10; and
p is an integer from 0 to 10).

That is, more specifically this alginic acid derivative is an alginic acid derivative represented by formula (AL-1-I) below, in which any one or more carboxyl groups of an alginate form amide bonds with the crosslinking group represented by formula (I) above:

[C30]

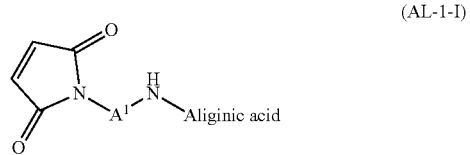
(AL-1-I)

[in formula (AL-1-I), the linker ($-A^1-$) is defined as above], or an alginic acid derivative represented by formula (AL-1-II) below, in which any one or more carboxyl groups of an alginate form amide bonds with the crosslinking group represented by formula (II) above:

[C31]

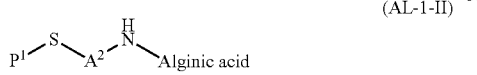
(AL-1-II)

[in formula (AL-1-II), $P^1$ and the linker ($-A^2-$) are defined as above].

To "have the group of formula (I)", be "substituted with the group of formula (I)", "have the group of formula (II)" or be "substituted with the group of formula (II)" here means that a carboxyl group in at least one selected from the group consisting of alginic acid, esters thereof, and salts thereof forms an amide bond with a terminal amino group of the group of formula (I) or the group of formula (II) (that is, with a spacer bound to a crosslinking group), thereby binding the at least one selected from the group consisting of alginic acid, esters thereof, and salts thereof with the crosslinking group via the spacer.

The group of formula (I) and/or formula (II) is introduced into an alginate by substitution at some of the carboxyl groups of at least one kind of alginate selected from the group consisting of alginic acid, esters thereof, and salts thereof (hereunder sometimes called an "alginate").

The weight-average molecular weight of the alginic acid derivative represented by formula (AL-1-I) or (AL-1-II) is preferably 100,000 Da to 3,000,000 Da, or more preferably 300,000 Da to 2,500,000 Da, or still more preferably 500,000 Da to 2,000,000 Da. The molecular weight of the alginic acid derivative can be determined by methods similar to those used for the alginate above.

Neither the crosslinking group represented by formula (I) in the alginic acid derivative represented by formula (AL-1-I) nor the crosslinking group represented by formula (II) in the alginic acid derivative represented by formula (AL-1-II) needs to be bound to all the carboxyl groups of the constituent units of the alginate.

In the alginic acid derivative represented by formula (AL-1-I) and the alginic acid derivative represented by formula (AL-1-II), the introduction rate of the group of formula (I) and the group of formula (II) in the respective alginic acid derivatives (that is, the crosslinking group introduction rate) is preferably 1% to 30%, or more preferably 2% to 15%, or still more preferably 3% to 10%.

In the alginic acid derivative represented by formula (AL-1-I) and the alginic acid derivative represented by formula (AL-1-II), the introduction rate of the group of formula (I) and the group of formula (II) in the respective alginic acid derivative (that is, the crosslinking group introduction rate) is given as a percentage value representing the number of uronic acid monosaccharide units having introduced crosslinking groups out of all of the uronic acid monosaccharide units that are repeating units of the alginate. Unless otherwise specified, the % value used as the introduction rate of the group represented by formula (I) or formula (II) in the alginic acid derivative (formula (AL-1-I) or formula (AL-1-II)) is a mol % value. The introduction rate of the group represented by formula (I) or formula (II) can be determined by the methods described in the examples below.

In this Description, the maleimide group in formula (AL-1-I) and the thiol group in formula (AL-1-II) form a covalent bond (sulfide bonds) by a Michael addition reaction, thereby forming a crosslink.

1.1 Crosslinking Group and Linker

In formula (I), the following partial structural formula (excluding the part to the right of the broken line in the formula):

[C32]

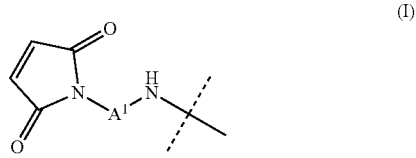
(I)

may be called a "crosslinking group" or a "reactive group".
Furthermore, $-A^1-$ may be called a "spacer" or a "linker".

The -A$^1$- spacer (linker) in formula (I) is selected from the group consisting of the following formulae (excluding the parts outside the broken lines at both ends of each formula):

[C33]

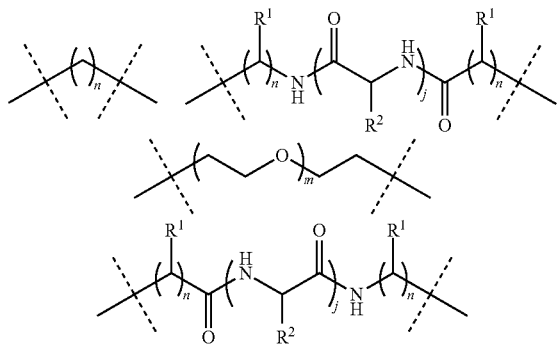

(however, -A$^1$-=—CH$_2$CH$_2$— is excluded in some embodiments);

more preferably, it is selected from the group consisting of the following formulae (excluding the part to the right of the broken line in each formula):

[C34]

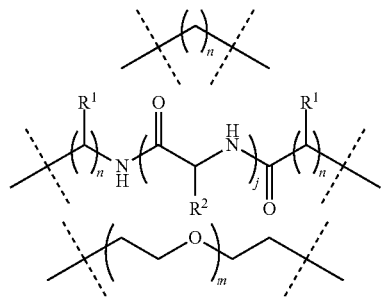

(however, -A$^1$-=—CH$_2$CH$_2$— is excluded in some embodiments).

The following formulae:

[C35]

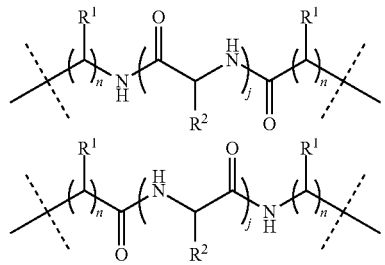

here encompass amino acids and peptide partial structures, and as discussed below, each R$^1$ and R$^2$ is a side chain (R) of the amino acid unit (—CO—(CHR)—NH—) or (—NH—(CHR)—CO).

(1) Hydrogen atom (glycine side chain)
(2) Methyl group (alanine side chain)
(3) Isopropyl group (valine side chain)
(4) Isobutyl group (leucine side chain)
(5) sec-butyl group (isoleucine side chain)
(6) Hydroxymethyl group (serine side chain)
(7) 2-hydroxyethyl group (threonine side chain)
(8) Thiolmethyl group (cysteine side chain)
(9) Methylthioethyl group (methionine side chain)
(10) Carboxymethyl group (aspartic acid side chain)
(11) Carboxyethyl group (glutamic acid side chain)
(12) Aminocarbonylmethyl group (asparagine side chain)
(13) Aminocarbonylethyl group (glutamine side chain)
(14) Aminobutyl group (lysine side chain)
(15) Guanidinopropyl group (arginine side chain)
(16) Benzyl group (phenylalanine side chain)
(17) 4-Hydroxybenzyl group (tyrosine side chain)
(18) 3-Indolylmethyl group (tryptophan side chain)
(19) 4-Imidazoylmethyl group (histidine side chain)
(20) Propane-1,3-diyl group forming a ring together with the carbon atom to which R$^1$ is bound and the nitrogen atom to which the carbon atom is bound (proline side chain)

In each of these embodiments, n is preferably an integer from 1 to 10, or more preferably an integer from 1 to 8, or still more preferably an integer from 3 to 6.

In each of these embodiments, m is preferably an integer from 1 to 7, or more preferably an integer from 1 to 5, or still more preferably an integer from 1 to 3, or particularly preferably 1 or 2.

In each of these embodiments, j is preferably an integer from 0 to 8, or more preferably an integer from 1 to 6, or still more preferably an integer from 2 to 4, or particularly preferably 0 or 1.

In this Description, the linker -A$^1$- in formula (I) encompasses the following formula (AL-A1-1) or (AL-A1-2) (excluding the parts outside the broken lines at both ends of each formula):

[C36]

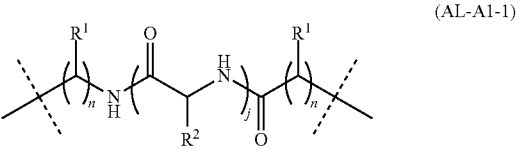
(AL-A1-1)

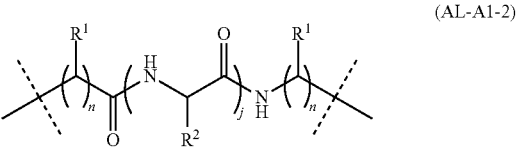
(AL-A1-2)

and when an asymmetric carbon exists in the formula, this means that all optical isomers thereof are included.

For example, when the linker -A$^1$- in formula (I) is the following formula (AL-A1-1-a) (excluding the parts outside the broken lines at both ends of each formula):

[C37]

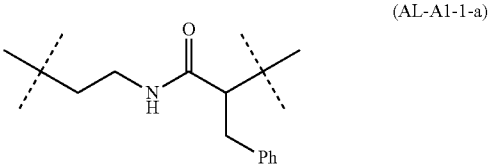
(AL-A1-1-a)

this means that the linkers represented by the following formula (AL-A1-1-aS) in which the carbon substituted by the benzyl group is in the S configuration and the following formula (AL-A1-1-aR) in which the carbon substituted by the benzyl group is in the R configuration:

[C38]

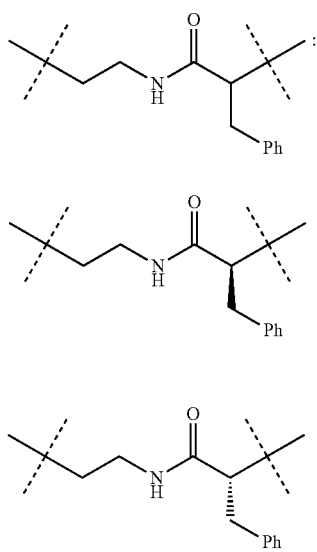

(AL-A1-1-a)

(AL-A1-1-aS)

(AL-A1-1-aR)

are included (excluding the parts outside the broken lines at both ends of each formula).

Also, for example formula (I) may be formula (I-x) (excluding the part to the right of the broken line in the formula):

[C39]

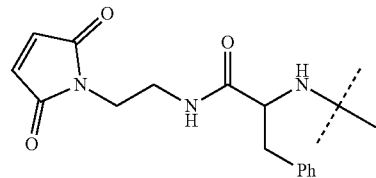

[I-x]

which has optical isomers, and unless otherwise specified, this means that the isomers represented as the S configuration (formula (I-x-S)) and R configuration (formula (I-x-R)) below are included.

[C40]

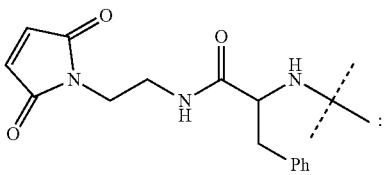

(I-x)

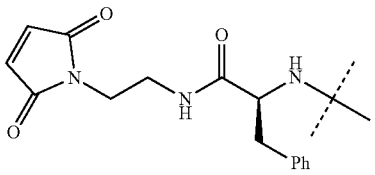

(I-x-S)

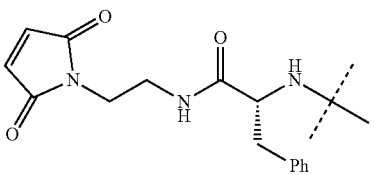

(I-x-R)

In the formula (I) of the present invention, when an asymmetric carbon is present in the linker -A1- (when it is optically active), the optically active forms can be separated from the racemate by ordinary optical splitting means (separation means) in the step of synthesis of the amine derivative (AM-1) corresponding to formula (I), or else each optically active form can by synthesized by using asymmetric synthesis to selectively synthesize one optical isomer in the step of synthesis of the amine derivative (AM-1) corresponding to formula (I). Using each of the resulting optically active amine derivatives, it is possible to synthesize an alginic acid derivative with an (optically active) introduced group of formula (I) having an asymmetric carbon.

Examples of the separation means include optical splitting methods such as fractional recrystallization, the diastereomer method, the chiral column method and the like. Each separation method is described in detail below.

Fractional recrystallization: An optical resolution agent is ionically bonded to the racemate to obtain crystalline diastereomers, the crystalline diastereomers are separated by fractional recrystallization, and the optical resolution agent is removed if desired to obtain optically pure compounds. Examples of the optical resolution agent include (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine and the like.

Diastereomer method: An optical resolution agent is covalently bonded to a racemic mixture to obtain a diastereomer mixture, after which the optically pure diastereomers are separated by ordinary separation methods (such as fractional recrystallization, silica gel column chromatography or HPLC), and the optical resolution agent is then removed by a chemical reaction (hydrolysis reaction or the like) to obtain optically pure optical isomers.

For example, when the compound of the invention or an intermediate compound has a hydroxyl group or (primary, secondary) amino group, ester or amide diastereomers can be obtained from each by a condensation reaction between the compound and an optically active organic acid (for example, α-methoxy-α-(trifluoromethyl)phenylacetic acid, (−)-methoxyacetic acid and the like). When the compound of the invention has a carboxyl group, amide or ester diastereomers can be obtained from each by a condensation reaction between the compound and an optically active amine or optically active alcohol. The diastereomers obtained from the condensation reaction are separated, and each diastereomer is subjected to a hydrolysis reaction with an acid or base to convert it into an optically pure optical isomer of the original compound.

Chiral column method: This is a method of direct optical splitting by subjecting a racemate or salt thereof to chromatography with a chiral column (optical isomer separation column).

In the case of high performance liquid chromatography (HPLC) for example, a mixture of optical isomers can be added to a chiral column (for example, Daicel Corporation, CHIRAL series), and developed with an elution solvent (a single solvent such as water, a buffer such as a phosphoric acid buffer, or an organic solvent such as ethanol, methanol, isopropanol, acetonitrile, trifluoroacetic acid or diethylamine, or a mixed solvent of these) to separate the optical isomers. Alternatively, optical isomers can also be separated by gas chromatography using a chiral column (for example, a CP-Chirasil-DeX CB (GL Sciences Inc.) or the like). In the case of supercritical fluid chromatography (SFC), on the other hand, a mixture of optical isomers can be added to a chiral column (for example, Daicel Corporation, CHIRAL series), and the optical isomers can then be separated using carbon dioxide and a suitable organic solvent (such as methanol, ethanol, isopropanol, trifluoroacetic acid or diethylamine) as elution solvents.

Examples of asymmetric synthesis methods for selectively synthesizing only one of the optical isomers include (1) asymmetric synthesis reactions for deriving optically active compounds by enantiomerically reacting racemic compounds, and (2) methods of diastero-selective synthesis from naturally occurring optically active compounds such as sugars and amino acids.

In the embodiments above, -A$^1$- is still more preferably selected from the group consisting of the following formulae (excluding the parts outside the broken lines at both ends of each formula):

[C41]

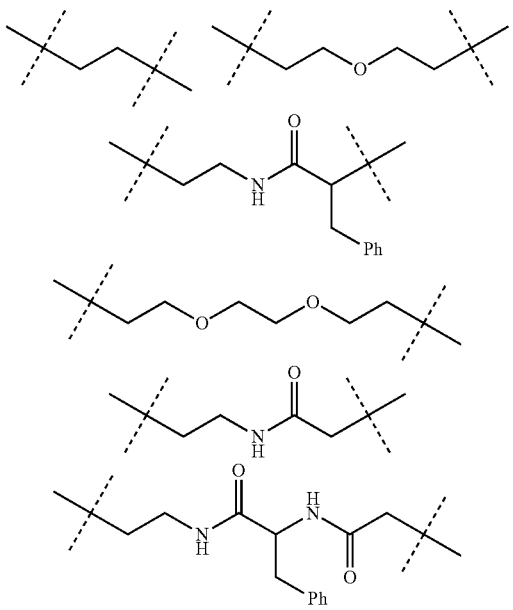

(however, -A$^1$-=—CH$_2$CH$_2$— is excluded in some embodiments).

In the embodiments above, A$^1$- is particularly preferably selected from the group consisting of the following formulae (excluding the parts outside the broken lines at both ends of each formula):

[C42]

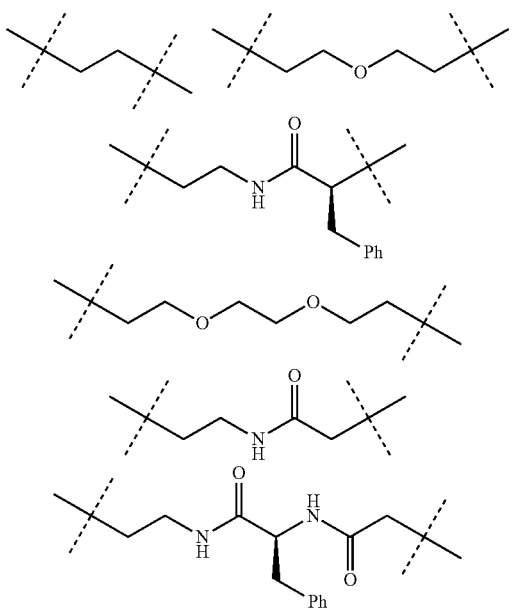

(however, -A$^1$-=—CH$_2$CH$_2$— is excluded in some embodiments).

More preferably, the group represented by formula (I) is selected from the group consisting of the following formulae (excluding the part to the right of the broken line in each formula):

[C43]

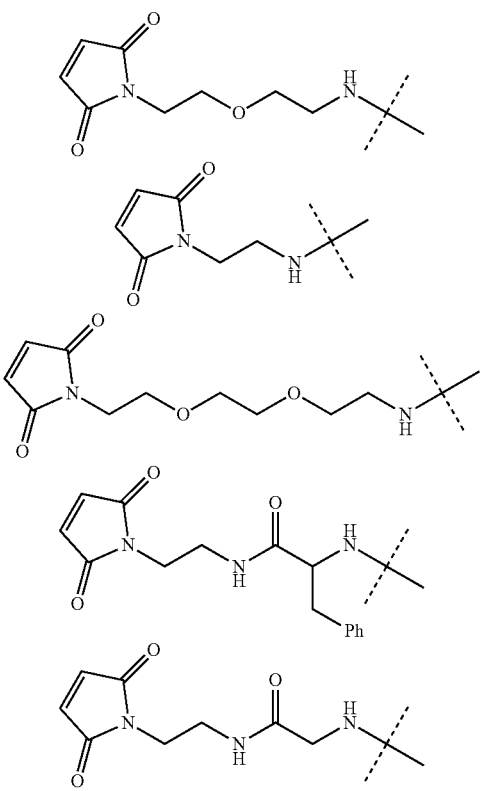

-continued

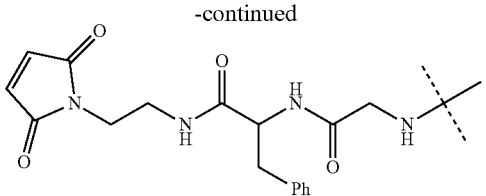

(however, the following formula (excluding the part to the right of the broken line) is excluded in some embodiments:

[C44]

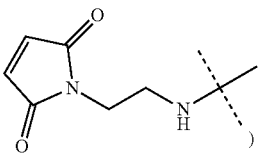

Still more preferably, the group represented by formula (I) is selected from the group consisting of the following formulae (excluding the part to the right of the broken line in each formula):

[C45]

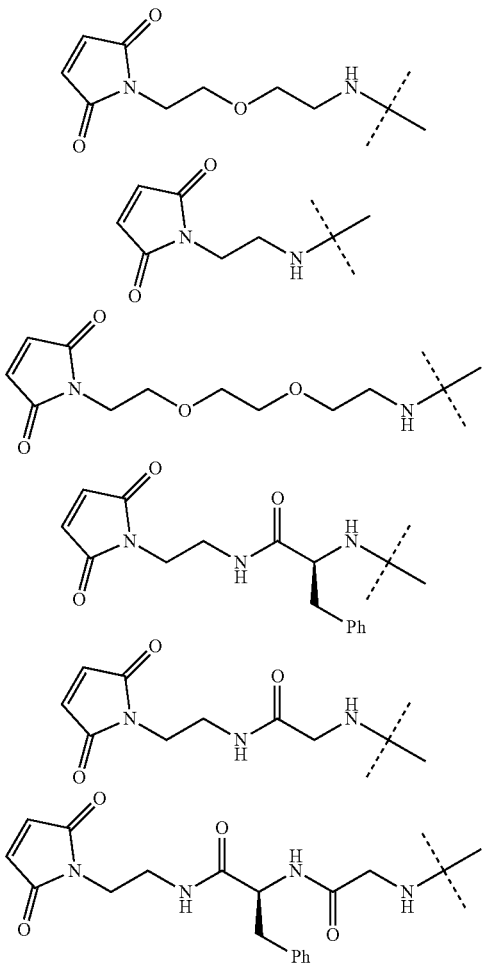

(however, the following formula (excluding the part to the right of the broken line) is excluded in some embodiments:

[C46]

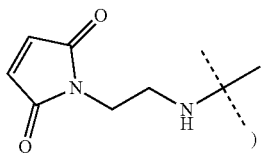

In the formula (II), the partial structure:

[C47]

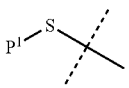

may be called a "crosslinking group" or a "reactive group", and -$A^2$- may be called a "spacer" or "linker".

$P^1$ in the crosslinking group of formula (II) is a hydrogen atom or a protecting group of a thiol (—SH) group. Examples of this protecting group include acetyl, benzoyl, triphenylmethyl, methoxymethyl and N-ethylcarbamate groups, of which an acetyl or benzoyl group is preferred, and an acetyl group is more preferred.

$P^1$ is preferably a hydrogen atom, an acetyl group or a benzoyl group, and more preferably is a hydrogen atom or an acetyl group.

The -$A^2$- linker of formula (II) is a linker represented by the following formula (excluding the parts outside the broken lines at both ends of the formula):

[C48]

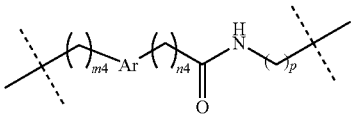

In each of the above embodiments, n4 is preferably an integer from 0 to 8, or more preferably an integer from 0 to 6, or still more preferably an integer from 0 to 2, or particularly preferably 0 or 2.

In each of the above embodiments, m4 is preferably an integer from 0 to 8, or more preferably an integer from 0 to 6, or still more preferably an integer from 0 to 2, or particularly preferably 1.

In each of the above embodiments, p is preferably an integer from 0 to 8, or more preferably an integer from 1 to 6, or still more preferably an integer from 2 to 4, or particularly preferably 2 or 3.

In each of the above embodiments, Ar is a phenylene group in which the water-soluble substituent is optionally substituted, such as for example an o-phenylene group, m-phenylene group or p-phenylene group, or preferably a p-phenylene group. In these embodiments, 1 to 4, or preferably 1 to 3, or more preferably 1 or 2 water-soluble substituents may be independently substituted in the phenylene group.

In this Description, a phenylene group is a polyvalent group obtained by removing two hydrogens from a benzene ring, and is represented as —C$_6$H$_4$—. A phenylene group may for example be an orthophenylene group (o-phenylene group) obtained by removing two hydrogen atoms in the ortho-position, a metaphenylene (m-phenylene) group obtained by removing two hydrogen atoms in the meta-position, or a paraphenylene (p-phenylene) group obtained by removing two hydrogen atoms in the para-position.

In this Description, a water-soluble substituent is a substituent such as a hydroxyl group (—OH), carboxyl group (—COOH), amino group (—NH$_2$), thiol group (—SH) or sulfo group (—SO$_2$OH), and hydroxyl and amino groups are preferred.

In each of the above embodiments, Ar is an unsubstituted phenylene group (such as an o-phenylene group, m-phenylene group or p-phenylene group, or preferably a p-phenylene group).

In each of the above embodiments, still more preferably -A$^2$- is a linker selected from the group consisting of the following formulae (excluding the parts outside the broken lines at both ends of each formula):

[C49]

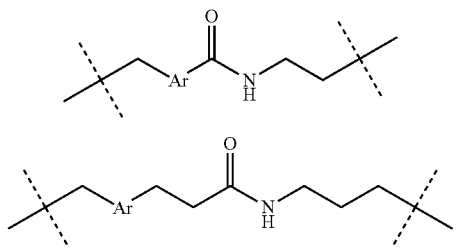

and —Ar— is a p-phenylene group.

More preferably, the group represented by formula (II) is selected from the group consisting of the following formulae (excluding the part to the right of the broken line in each formula):

[C50]

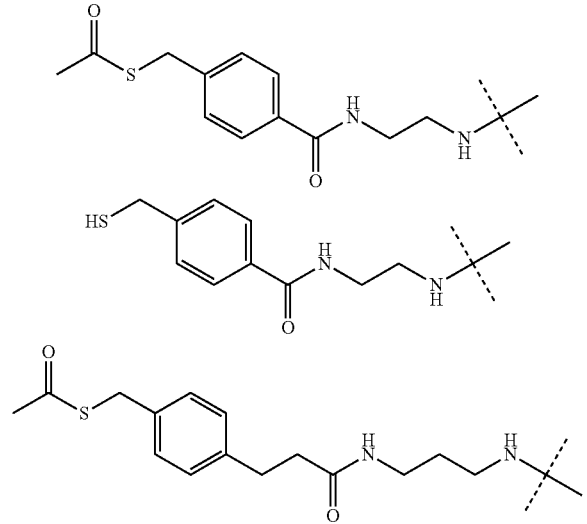

Still more preferably, the group represented by formula (II) is selected from the group consisting of the following formulae (excluding the part to the right of the broken line in each formula):

[C51]

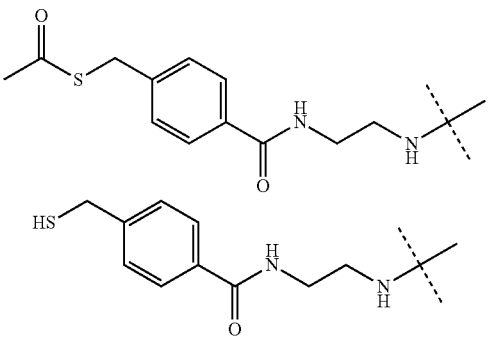

In some embodiments, the crosslinking group (reactive group) of formula (I) and/or formula (II) may be any group that forms a Michael adduct by a Michael reaction as long as the group allows a crosslinking reaction to progress. Due to the introduction of the spacer (linker), the crosslinking reaction also progresses even when the introduction rate of the crosslinking group is low. The crosslinking reaction causes the alginic acid derivative to form a three-dimensional mesh structure via crosslinks. In a preferred alginic acid derivative, the stability after crosslinking is greater than before crosslinking.

1.2 Alginate

The alginate used may be either naturally derived or synthetic but is preferably naturally derived. A preferred alginate is a bioabsorbable polysaccharide that is extracted from brown algae such as *Lessonia, Macrocystis, Laminaria, Ascophyllum, Durvillea, Ecklonia cava, Eisenia bicyclis* and *Saccharina japonica*, and is a polymer resulting from linear polymerization of two kinds of uronic acid, D-mannuronic acid (M) and L-guluronic acid (G). More specifically, it is a block copolymer including a homopolymer fraction of D-mannuronic acid (MM fraction), a homopolymer fraction of L-guluronic acid (GG fraction), and a fraction of randomly arranged D-mannuronic acid and L-guluronic acid (M/G fraction) in arbitrary combination. Descriptions of the alginate in this Description pertain to at least one kind of alginic acid selected from the group consisting of alginic acid, the alginic acid, esters thereof, and salts thereof (such as sodium alginate).

In this Description, the molecular weights of alginic acid, alginic acid derivatives and crosslinked alginic acid are described in units of Da (Daltons).

The constituent ratio of D-mannuronic acid and L-guluronic acid in an alginate differs mainly according to the seaweed or other organism from which it is derived, and may also be affected by the organism's habitat and the season, with a wide range from high-G (M/G ratio about 0.2) to high-M alginic acid (M/G ratio about 5). The gelling ability of the alginate and the properties of the resulting gel are affected by the M/G ratio, and in general, the gel strength is known to be greater the higher the G proportion. The M/G ratio also affects the hardness, fragility, water absorption, flexibility and the like of the gel. The M/G ratio of the alginate and/or salt thereof that is used is normally from 0.2 to 4.0, or more preferably from 0.4 to 3.0, or still more preferably from 0.5 to 3.0.

When numerical ranges are indicated with "from" and "to" this Description, the numbers after "from" and "to" are the minimum and maximum values of the range, respectively.

When used in this Description, an "alginic acid ester" or "alginic acid salt" is not particularly limited, but because it will react with a crosslinking agent, it must have no functional groups that would impede the crosslinking reaction. Desirable examples of alginic acid esters include propylene glycol alginate and the like.

Examples of alginic acid salts include monovalent and divalent salts of alginic acid.

Preferred examples of monovalent alginic acid salts include sodium alginate, potassium alginate and ammonium alginate, of which sodium alginate and potassium alginate are more preferred, and sodium alginate is especially preferred.

Preferred examples of divalent alginic acid salts include calcium alginate, magnesium alginate, barium alginate, strontium alginate and the like.

Alginates are high-molecular-weight polysaccharides, the molecular weights of which hard to determine accurately, but generally the weight-average molecular weight is in the range of 1,000 to 10,000,000, or preferably 10,000 to 8,000,000, or more preferably 20,000 to 3,000,000. It is known that in molecular weight measurement of naturally derived high-molecular-weight substances, values may differ depending on the measurement method.

For example, the weight-average molecular weight as measured by gel permeation chromatography (GPC) or gel filtration chromatography (which together are also called size exclusion chromatography) is preferably at least 100,000, or more preferably at least 500,000, and is preferably not more than 5,000,000, or more preferably not more than 3,000,000. The preferred range is 100,000 to 5,000,000, or more preferably 150,000 to 3,000,000.

The absolute weight-average molecular weight can also be measured by the GPC-MALS method for example. The weight-average molecular weight (absolute molecular weight) as measured by the GPC-MALS method is preferably at least 10,000, or more preferably at least 50,000, or still more preferably at least 60,000, and is preferably not more than 1,000,000, or more preferably not more than 800,000, or still more preferably not more than 700,000, or especially not more than 500,000. The preferred range is 10,000 to 1,000,000, or more preferably 50,000 to 800,000, or still more preferably 60,000 to 700,000, or particularly preferably 60,000 to 500,000.

When the molecular weight of a high-molecular-weight polysaccharide is measured by such methods, a measurement error of 10% to 20% is normal. Thus, a value given as 400,000 may vary in the range of 320,000 to 480,000, a value given as 500,000 may vary in the range of 400,000 to 600,000, and a value given as 1,000,000 may vary in the range of 800,000 to 1,200,000 for example.

The molecular weight of the alginate can be measured by ordinary methods.

Typical conditions for molecular weight measurement using gel filtration chromatography are described in the examples of this Description below. For example, a Superose 6 Increase 10/300 GL column (GE Health Care Sciences) may be used as the column, a 10 mmol/L phosphoric acid buffer (pH 7.4) containing 0.15 mol/L NaCl may be used as the development solvent, and blue dextran, thyroglobulin, ferritin, aldolase, conalbumin, ovalbumin, ribonuclease A and aprotinin may be used as molecular weight standards.

The viscosity of the alginate used in this Description is not particularly limited, but when measured in a 1 w/w % aqueous alginate solution, it is preferably 10 mPa·s to 1,000 mPa·s, or more preferably 50 mPa·s to 800 mPa·s.

The viscosity of the aqueous alginate solution can be measured by ordinary methods. For example, it can be measured by rotational viscometry using a coaxial double cylindrical rotational viscometer, single cylindrical rotary viscometer (Brookfield viscometer), conical plate rotational viscometer (cone plate viscometer) or the like. Preferably it is measured following the viscosity measurement methods of the Japanese Pharmacopoeia (16th Edition). More preferably, a cone plate viscometer is used.

When first extracted from brown algae, alginates have a high molecular weight and a high viscosity, but the molecular weight and viscosity are reduced by the processes of heat drying, purification and the like. Using methods such as controlling the temperature and other conditions during the manufacturing process, selecting the brown algae used as raw materials, and fractioning the molecular weights in the manufacturing process, it is possible to manufacture alginates with different molecular weights. An alginate having the desired molecular weight can also be obtained by mixing alginates from different lots having different molecular weights or viscosities.

In some embodiments the alginate used here is not low endotoxin, while in other embodiments that alginate is low endotoxin. "Low endotoxin" means that the level of endotoxins is so low that there is no effective risk of inflammation or fever. An alginate that has been subjected to low endotoxin treatment is more preferred.

Low endotoxin treatment can be performed by known methods or analogous methods. For example, it can be performed by the methods of Kan et al for purifying sodium hyaluronate (see for example Japanese Patent Application Publication No. JP H09-324001A, etc.), the methods of Yoshida et al for purifying β 1,3-glucan (see for example Japanese Patent Application Publication No. JP H08-269102A), the methods of William et al for purifying biopolymer salts such as alginate and gellan gum (see for example Japanese Patent Application Publication No. JP 2002-530440A), the methods of James et al for purifying polysaccharides (see for example PCT Publication WO 93/13136A1, pamphlet), the methods of Lewis et al (see for example U.S. Pat. No. 5,589,591A), and the methods of Herman Frank for purifying alginate (see for example Appl. Microbiol. Biotechnol. (1994) 40: 638-643, etc.) and the like or analogous methods. Low endotoxin treatment is not limited to these methods, and may also be performed by known methods such as washing, filtration with a filter (endotoxin removal filter, charged filter or the like), ultrafiltration, column purification (using an endotoxin adsorption affinity column, gel filtration column, ion-exchange resin column or the like), adsorption by a hydrophobic substance, resin, activated carbon or the like, organic solvent treatment (organic solvent extraction, deposition/sedimentation with an organic solvent or the like), surfactant treatment (see for example Japanese Patent Application Publication No. JP 2005-036036A) or the like, or by a suitable combination of these methods. Known methods such as centrifugation may also be combined with the steps of such treatment. The treatment is preferably selected appropriately according to the type of alginic acid.

The endotoxin level can be confirmed by known methods, such as limulus reagent (LAL) methods or methods using an Endospecy (registered trademark) ES-24S set (Seikagaku Corp.).

There are no particular limitations on the endotoxin treatment method used, but the resulting endotoxin content of the treated alginate is preferably not more than 500 endotoxin units (EU)/g, or more preferably not more than 100 EU/g, or still more preferably not more than 50 EU/g, or especially not more than 30 EU/g when measured with a limulus reagent (LAL). Low endotoxin treated sodium alginate is available as a commercial product such as Sea Matrix (registered trademark) (Mochida Pharmaceutical) or PRONOVA (trademark) UP LVG (FMC BioPolymer).

1.3 Composition

A composition containing at least one kind of alginic acid derivative represented by formula (AL-1-I) below in which any one or more carboxyl groups of an alginate form amide bonds with a crosslinking group represented by formula (I) above and at least one kind of alginic acid derivative represented by formula (AL-1-II) below in which any one or more carboxyl groups of an alginate form amide bonds with a crosslinking group represented by formula (II) above is provided here. The embodiments of the linker (-$A^1$-) in the formula (AL-1-I) and the embodiments of the linker (-$A^2$-) and $P^1$ in the formula (AL-1-II) are as described above.

[C52]

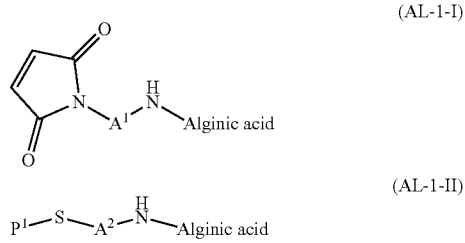

In the composition of some embodiments, the weight ratio of the alginic acid derivative of formula (AL-1-I) to the alginic acid derivative of formula (AL-1-II) (alginic acid derivative of (AL-1-I):alginic acid derivative of (AL-1-II)) is from 1:1 to 1.5 for example, or preferably 1:1.2 to 1.5, or 1:1 to 1.2, or more preferably 1:1.

In the composition of some embodiments, the weight ratio of the alginic acid derivative of formula (AL-1-II) to the alginic acid derivative of formula (AL-1-I) (alginic acid derivative of (AL-1-II) alginic acid derivative of (AL-1-I)) is from 1:1 to 1.5 for example, or preferably 1:1.2 to 1.5, or 1:1 to 1.2, or more preferably 1:1.

In the composition of some embodiments, the mixing ratio of the alginic acid derivative of formula (AL-1-I) to the alginic acid derivative of formula (AL-1-II) based on the introduction rates (mol %) of the crosslinking groups (reactive groups) of the alginic acid derivative of formula (AL-1-I) and the alginic acid derivate of formula (AL-1-II) is from 1:1 to 1.5, or preferably 1:1.2 to 1.5, or 1:1 to 1.2, or more preferably 1:1.

In the composition of some embodiments, the mixing ratio of the alginic acid derivative of formula (AL-1-II) to the alginic acid derivative of formula (AL-1-I) based on the introduction rates (mol %) of the crosslinking groups (reactive groups) of the alginic acid derivative of formula (AL-1-II) and the alginic acid derivate of formula (AL-1-I) is from 1:1 to 1.5, or preferably 1:1.2 to 1.5, or 1:1 to 1.2, or more preferably 1:1.

1.4 Crosslinked Alginic Acid Structure

The crosslinked alginic acid structure is a three-dimensional mesh structure formed by the alginic acid derivative of formula (AL-1-I), the alginic acid derivative of formula (AL-1-II) or a mixture of these (sometimes called simply the "alginic acid derivative") via crosslinking groups. The crosslinked alginic acid structure can be obtained by performing a crosslinking reaction on an alginic acid derivative having a crosslinking group. The crosslinking reaction may be performed by the methods described below or a combination of these methods for example, but these are not limitations:

(a) A crosslinking reaction (covalent binding crosslinking reaction) in which a composition containing the alginic acid derivative of formula (AL-1-I) is reacted with a composition containing the alginic acid derivative of formula (AL-1-II) or (b) A crosslinking reaction (ionic binding crosslinking reaction) in which a composition containing the alginic acid derivative of formula (AL-1-I) or the alginic acid derivative of formula (AL-1-II) is reacted in a solution containing a divalent metal ion (such as a calcium ion, barium ion or the like), or (c) A crosslinking reaction (covalent binding crosslinking reaction+ionic binding crosslinking reaction) in which a composition containing the alginic acid derivative of formula (AL-1-I) and the alginic acid derivative of formula (AL-1-II) is reacted in a solution containing a divalent metal ion (such as a calcium ion, barium ion or the like).

Methods for preparing the crosslinked alginic acid structure are described under 2.2 below.

The shape of the crosslinked alginic acid structure is not particularly limited, but for example it may be in the form of a tube structure, fibrous structure, fiber, bead, gel, nearly spherical gel, microcapsule or the like, and a fiber, bead or nearly spherical gel is preferred.

A preferred crosslinked alginic acid structure is one having improved stability. The crosslinked alginic acid structure may also have the ability to retain contents within the structure (content retention property).

The stability of the crosslinked alginic acid structure can be confirmed for example by measuring gel stability, measuring the gel leak rate or the like.

Gel stability can be determined as follows. Phosphate buffered saline (PBS) is added to a crosslinked alginic acid structure gel in a container, and the concentration (μg/ml) of alginic acid eluted into the PBS is measured. The measured alginic acid concentration divided by the total alginic acid concentration obtained by decomposing the crosslinked alginic acid structure gel is given as a percentage and used as the collapse rate. Specifically, gel stability can be determined by the methods described in the examples below. The gel collapse rate of the crosslinked alginic acid structure is preferably 0% to 90%, or more preferably 0% to 70%, or still more preferably 0% to 50%. The stability of the crosslinked alginic acid structure is higher the lower the concentration of alginic acid eluted into an aqueous solution, or in other words the lower the gel collapse rate.

The gel leak rate can be determined as follows. A crosslinked alginic acid structure gel containing fluorescein isothiocyanate-dextran is prepared, phosphate buffered saline (PBS) is added to the gel in a container, and the concentration of dextran leaking into the PBS is measured. The measured dextran concentration divided by the total dextran concentration obtained by decomposing the fluorescein isothiocyanate-dextran-containing crosslinked alginic acid structure gel is given as a percentage and used as the gel leak rate. Specifically, the gel leak rate can be determined by the methods described in the examples below. The gel leak rate 48 hours after addition of PBS to the crosslinked alginic acid derivative is preferably 0% to 90%, or more preferably 0% to 70%, or still more preferably 0% to 50%. The stability of the crosslinked alginic acid derivative is greater the lower the gel leak rate.

The crosslinked alginic acid structure gel containing fluorescein isothiocyanate-dextran was prepared as follows. A crosslinked alginic acid structure gel containing fluorescein isothiocyanate-dextran can be obtained by mixing a solution of an alginic acid derivative having a crosslinking group with a fluorescein isothiocyanate-dextran solution, dripping this mixed solution into a solution containing a calcium ion, and leaving the resulting gel in the solution for 10 minutes at 37° C. to cause a crosslinking reaction.

2. Method for Synthesis of Alginic Acid Derivative

The alginic acid derivative can be obtained by a condensation reaction between the terminal amino group of a linker having an introduced crosslinking group (reactive group) and a carboxyl group of an alginate.

Specifically, an alginic acid derivative represented by formula (AL-1-I) or (AL-1-II) can be manufactured by a condensation reaction in which a condensing agent is used to react an amine derivative represented by formula (AM-I) (in which -A$^1$- is defined as in some of the embodiments above) or an amine derivative represented by formula (AM-II) (in which P$^1$ and -A$^2$- are defined as in some of the embodiments above) with any carboxyl group of an alginate.

[C53]

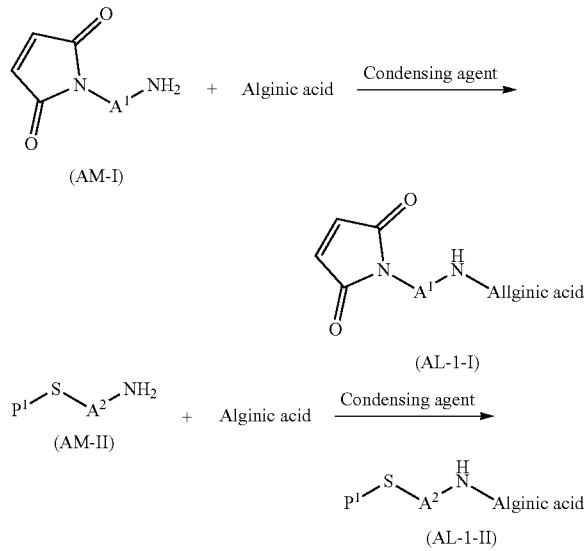

[Method for Preparing Alginic Acid Derivative of (AL-1-I)]

Using an 0.5 wt % to 1 wt % aqueous alginic acid solution and the amino derivative represented by formula (AM-I), the alginic active derivative of formula (AL-1-I) can be manufactured by methods known in the literature (for example, "Experimental Chemistry Course 5th Edition, Vol. 16, Synthesis of Organic Compounds IV: Carboxylic acids, derivatives and esters", pp. 35-70, "Acid amides and acid imides", pp. 118-154, "Amino acids and peptides", pp. 258-283, 2007 (Maruzen)) by performing a condensation reaction at temperatures between 0° C. and 50° C., with or without an inorganic base such as sodium hydrogen carbonate or sodium carbonate or an organic base such as triethylamine or pyridine, in a mixed solvent of water and a solvent selected from the ether solvents such as tetrahydrofuran and 1,4-dioxane, the alcohol solvents such as methanol, ethanol and 2-propanol and the polar solvents such as N,N-dimethylformamide and the like to a degree that does not cause precipitation of the alginic acid, in the presence of a condensing agent selected from 1,3-dicyclohexyl carbodiimide (DCC), 1-ethyl-3-(3-dimethylaminopropyl) carbodiimide hydrochloride (WSC.HCl), benzotriazol-1-yloxytris(dimethylamino) phosphonium hexafluorophosphate (BOP reagent), bis(2-oxo-3-oxazolidinyl) phosphinic chloride (BOP—Cl), 2-chloro-1,3-dimethylimidazolinium hexafluorophosphate (CIP) or 4-(4,6-dimethoxy-1,3,5-triazin-2-yl)-4-methyl morpholinium chloride (DMT-MM).

[Method for Preparing Alginic Acid Derivative of Formula (AL-1-II)]

The alginic acid derivative of formula (AL-1-II) can be manufactured by a reaction conforming to the "Method for preparing alginic acid derivative of (AL-1-I)" above using an 0.5 wt % to 1 wt % aqueous alginic acid solution and the amino derivative represented by formula (AM-II).

In the above method for preparing the alginic acid derivative of formula (AL-1-I) or the alginic acid derivative of formula (AL-1-II), the introduction rate of the amino derivative of formula (AM-I) or formula (AM-II) can be adjusted by appropriately selecting and combining the reaction conditions in (i) to (v) below for example in consideration of the properties of the amino derivative and the like: (i) increasing or decreasing the equivalent amount of the condensing agent, (ii) raising or lowering the reaction temperature, (iii) lengthening or shortening the reaction time, (iv) adjusting the concentration of the alginic acid reaction substrate, (v) adding an organic solvent miscible with water to raise the solubility of the amino derivative of formula (AM-1) or (AM-2), etc.

When P$^1$ in formula (AL-1-II) is a thiol protecting group (acetyl group, benzoyl group or the like), an 0.5 wt % to 1 wt % aqueous solution of the thiol protected alginic acid derivative can be hydrolyzed at 0° C. to 30° C. with an inorganic base such as sodium hydroxide or potassium hydroxide in an excess amount relative to the introduced protected thiol group to manufacture an alginic acid derivative with an introduced thiol group (in which P$^1$ in formula (AL-1-II) is a hydrogen atom), and the resulting solution can be used as is in the crosslinking reaction after the excess base has been neutralized.

Methods for manufacturing the amino derivative represented by formula (AM-I) or (AM-II) are shown below.

2.1 Synthesis of Amino Derivatives 2.1.1 Synthesis of Amino Derivative of Formula (AM-I) (Reaction Formula A)

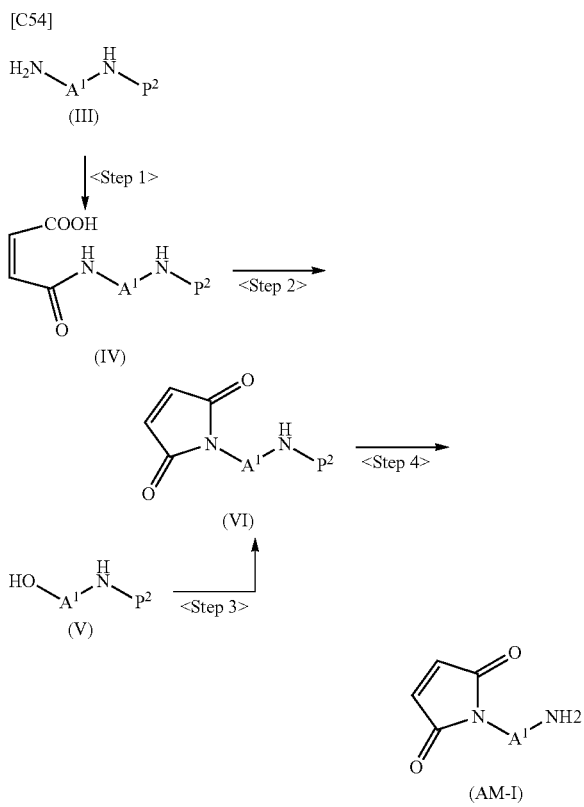

(Reaction Formula A) <Step 1>

Using the amine represented by formula (III) [the compound of formula (III) is a commercial compound or a compound that can be manufactured from commercial compounds by methods known in the literature; $P^2$ in the formula is an amino group protecting group, which can be selected appropriately], the compound of formula (IV) can be manufactured by methods known in the literature (for example, "Experimental Chemistry Course 5th Edition, Vol. 16, Synthesis of Organic Compounds IV: Carboxylic acids, and derivatives, acid amides and acid imides", pp. 146-154, 2007 (Maruzen)) by performing a reaction at temperatures between 0° C. and 50° C. with or without an inorganic base such as sodium hydrogen carbonate or sodium carbonate or an organic base such as triethylamine or pyridine in a solvent such as an ether solvent such as 1,4-dioxane, a halogen solvent such as methylene chloride, a polar solvent such as N,N-dimethylformamide in the presence of maleic acid and a condensing agent such as 1,3-dicyclohexyl carbodiimide (DCC), 1-ethyl-3-(3'-dimethylaminopropyl) carbodiimide hydrochloride (WSC.HCl), benzotriazol-1-yloxytris(dimethylamino) phosphonium hexafluorophosphate (BOP reagent), bis(2-oxo-3-oxazolidinyl) phosphinic chloride (BOP—Cl), 2-chloro-1,3-dimethylimidazolinium hexafluorophosphate (CIP) or 4-(4,6-dimethoxy-1,3,5-triazin-2-yl)-4-methyl morpholinium chloride (DMT-MM).

The compound of formula (IV) can also be manufactured by reacting maleic acid anhydride and the amine represented by formula (III) in a solvent such as methanol, ethanol or another alcohol solvent with or without a base such as triethylamine.

(Reaction Formula A) <Step 2>

The compound of formula (VI) can be manufactured by heating the monoamide represented by formula (IV) from 40° C. to the reflux temperature of the solvent (such as 100° C.) with a base such as sodium acetate in a solvent that does not affect the reaction, such as an ether solvent such as 1,4-dioxane, a hydrocarbon solvent such as toluene or a halogen solvent such as 1,2-dichloroethane, or in an acetic anhydride solvent, and the compound of formula (VI) can be manufactured by a cyclization process using a base such as sodium acetate in acetic anhydride without separating the monoamide after performing the operations of <Step 1>.

The compound of formula (VI) can also be manufactured by using a suitable condensing agent to derive an active ester.

(Reaction Formula A) <Step 3>

The compound of formula (VI) can be manufactured by reacting the alcohol represented by formula (V) [the compound of formula (V) is a commercial compound or a compound that can be manufactured from commercial compounds by methods known in the literature] and maleimide (1H-pyrrole-2,5-dione) at temperatures from −78° C. to about room temperature in the presence of a phosphine reagent such as triphenyl phosphine in a solvent such as an ether solvent such as tetrahydrofuran or a hydrocarbon solvent such as toluene with a Mitsunobu reagent such as diethyl azodicarboxylic acid or diisopropyl azodicarboxylate.

(Reaction Formula A) <Step 4>

The protected compound represented by formula (VI) can be deprotected by methods known in the literature, such as the methods described for example in "Experimental Chemistry Course 5th Edition, Vol. 16, Synthesis of Organic Compounds IV: Amino acids and peptides" pp. 258-283, 2007 (Maruzen) or the like, or deprotected by deprotection methods described in books such as Greene et al, "Protective Groups in Organic Synthesis", 4th Edition, 2007 (John Wiley & Sons) to manufacture the compound of formula (AM-I).

$P^2$ in the method for preparing the amine derivative of formula (AM-I) is an amino group protecting group selected from a —C(O)O-tert-Bu group, a —C(O)O-Bn group, a —C(O)CH$_3$ group, a —C(O)CF$_3$ group, a —SO$_2$Ph group, a —SO$_2$PhMe group, a —SO$_2$Ph(NO$_2$) group and the like.

For example, when P' is a tert-butoxycarbonyl (—C(O)O-tert-Bu) group, it can be deprotected using an acid such as hydrogen chloride or trifluoroacetic acid. Ethyl acetate, cyclopentyl methyl ether, or 1,4-dioxane containing hydrogen chloride may also be used. Trifluoroacetic acid may also be used without a solvent or with a solvent such as methylene chloride or toluene that is inactive in acid.

The amine of formula (AM-I) may also be obtained as necessary in the form of a salt such as a hydrochloride salt or trifluoroacetate salt.

2.1.2 Synthesis of Amine Derivative of Formula (AM-II) (Reaction Formula B)

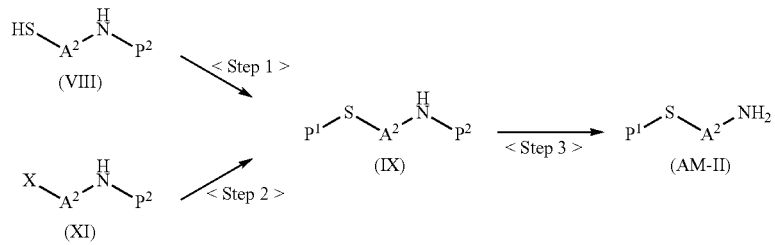

(Reaction B) <Step 1>

Using the thiol body represented by formula (VIII) [the compound of formula (VIII) is a commercial compound or a compound that can be manufactured from commercial compounds by methods known in the literature; $P^2$ in the formula is an amino group protecting group, which can be selected appropriately] the thiol protected compound of formula (IX) can be manufactured by methods known in the literature (such as "Protective Groups in Organic Synthesis, 3rd Edition, Protection for the thiol group", pp. 457-486, 1999) by reacting an acid halide such acetyl chloride or benzoyl chloride, an alkyl halide such as triphenyl methyl chloride or an isocyanate such as ethyl isocyanate with or without an organic base such as triethylamine or pyridine or an inorganic base such as potassium bicarbonate in a solvent that is inactive in the reaction, such as an ether solvent such as 1,4-dioxane or a halogen solvent such as methylene chloride, or by reacting it with a carboxylic acid derivative in a suitable condensing agent or acid catalyst.

(Reaction Formula B) <Step 2>

The compound of formula (IX) can be manufactured by reacting the halogen substituted body (X=Cl, Br, I) represented by formula (XI) [the compound of formula (XI) is a commercial compound or a compound that can be manufactured from commercial compounds by methods known in the literature; $P^2$ in the formula is an amino group protecting group, which can be selected appropriately] with an acylthio derivative such as thiobenzoic acid, thioacetic acid or potassium thioacetate in a solvent such as acetonitrile, methylene chloride or N,N-dimethylformamide that is inactive in the reaction, with or without a base such as potassium carbonate.

(Reaction Formula B) <Step 3>

The N-protected compound represented by formula (IX) can be deprotected by methods known in the literature, such as the methods described for example in "Experimental Chemistry Course 5th Edition, Vol. 16, Synthesis of Organic Compounds IV: Amino acids and peptides" pp. 258-283, 2007 (Maruzen) or the like, or deprotected by deprotection methods described in books such as Greene et al, "Protective Groups in Organic Synthesis", 4th Edition, 2007 (John Wiley & Sons) to manufacture the compound of formula (AM-II).

$P^2$ in the method for preparing the amine derivative of formula (AM-II) is an amino group protecting group selected from a —C(O)O-tert-Bu group, a —C(O)O-Bn group, a —C(O)CH$_3$ group, a —C(O)CF$_3$ group, a —SO$_2$Ph group, a —SO$_2$PhMe group, a —SO$_2$Ph(NO$_2$) group and the like.

For example, when P' is a tert-butoxycarbonyl (—C(O)O-tert-Bu) group, it can be deprotected using an acid such as hydrogen chloride or trifluoroacetic acid. Ethyl acetate, cyclopentyl methyl ether, or 1,4-dioxane containing hydrogen chloride may also be used. Trifluoroacetic acid may also be used without a solvent or with a solvent such as methylene chloride or toluene that is inactive in acid.

The amine of formula (AM-II) may also be obtained as necessary in the form of a salt such as a hydrochloride salt or trifluoroacetate salt.

2.2 Preparing Crosslinked Alginic Acid Structure

The crosslinked alginic acid structure can be obtained by a method that includes applying the crosslinking reaction described above to an alginic acid derivative having a crosslinking group. Specifically, it may be prepared by the following methods, but this is not a limitation.

(a) Coating Method

A solution containing the above alginic acid derivative of formula (AL-1-I) is partially crosslinked by dripping it into a solution containing a divalent metal ion, to obtain a specific structure. The gel or other structure obtained above can then be added to a solution containing the above alginic acid derivative of formula (AL-1-II) to perform a further crosslinking reaction on the surface or the like of structure and obtain a crosslinked alginic acid structure. This method can also be implemented using the alginic acid structure of formula (AL-1-I) in place of the alginic acid structure of formula (AL-1-II) and the alginic acid structure of formula (AL-1-II) in place of the alginic acid structure of formula (AL-1-I).

(b) Mixing Method

A solution containing the alginic acid derivative of formula (AL-1-I) above is mixed with a solution containing the alginic acid derivative of formula (AL-1-II) above, and this mixed solution is partially crosslinked by dripping it into a solution containing a divalent metal ion or the like to obtain a specific structure that is a crosslinked alginic acid structure.

Specific examples of the divalent metal ion used in these methods include calcium ions, magnesium ions, barium ions, strontium ions, zinc ions and the like, and a calcium ion is preferred. The calcium ion concentration of the solution containing the calcium ion is not particularly limited but may be 1 mM to 1 M for example, or preferably 5 mM to 500 mM, or more preferably 10 mM to 300 mM.

The solvent or solution used in the crosslinking reaction is not particularly limited: examples include ultrapure water, cell culture medium, phosphate buffered saline (PBS) and physiological saline, and ultrapure water is preferred. The specific structure may be in the form of a tube structure, fibrous structure, fiber, bead, gel, nearly spherical gel, microcapsule or the like.

3. Use for Alginic Acid Derivative and Crosslinked Alginic Acid Structure

The alginic acid derivative may be used in place of conventional alginic acid in a wide range of fields include foodstuffs, medicine, cosmetics, fibers, paper and the like. Specifically, preferred applications of the alginic acid derivative or crosslinked alginic acid structure include medical materials such as wound dressings, postoperative adhesion prevention materials, sustained drug release materials, cell culture substrates and cell transplant substrates.

When used as a medical material, the crosslinked alginic acid structure may be in the form of a tube, fiber, bead, gel, nearly spherical gel or the like; a bead, gel or nearly spherical gel is preferred, and a nearly spherical gel is more preferred.

The entire contents of all literature and publications cited in this Description, such as documents of prior art and patent documents including patent gazettes and published gazettes, are incorporated by reference in this Description. The priority claim for this application is based on Japanese Patent Application No. 2018-062201 (Mar. 28, 2018), and the present Description encompasses the matter disclosed in the Claims, Description and drawings of that application.

Moreover, the objectives, features, advantages and ideas of the present invention are clear to a person skilled in the art from the descriptions of this Description, and the present invention can be easily implemented by a person skilled in the art based on the descriptions of this Description. The best mode and specific examples for implementing the invention are used to illustrate preferred embodiments of the present invention, and the present invention is not limited to these because they are given for purposes of example or explanation. Based on the descriptions of this Description, a person skilled in the art can understand that various modifications are possible within the intent and scope of the present invention as disclosed in this Description.

EXAMPLES

A JEOL JNM-ECX400 FT-NMR (JEOL) was used for nuclear magnetic resonance (NMR) spectrum measurement.

In the NMR signal patterns of the $^1$H-NMR data, s means a singlet, d a doublet, t a triplet, q a quartet and m a multiplet, br means broad, J is the coupling constant, Hz means hertz, CDCl$_3$ is deuterated chloroform, DMSO-d$_6$ is deuterated dimethylsulfoxide, and D$_2$O is deuterium. In the $^1$H-NMR data, signals that cannot be confirmed because they are broadband, such as protons of hydroxyl (OH), amino (NH$_2$) and carboxyl (COOH) groups, are not included in the data.

"Room temperature" in the examples normally indicates a temperature from 0° C. to about 35° C.

In the examples, the "introduction rate" was measured by $^1$H-NMR in D$_2$O, and given as "mol % (NMR integration ratio)" based on the ratio of the proton integration values of the alginic acid and the reactive substituent (maleimide group) or aromatic ring.

Example 1

Synthesis of Alginic Acid (AL-EX-1) Having Introduced 2-(2,5-dioxo-2,5-dihydro-1H-pyrrole-1-yl) ethylamino Group

[C56]

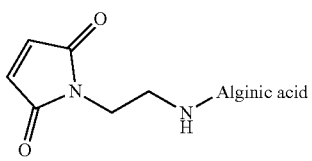
(AL-EX-1)

<Step 1>

Synthesis of tert-butyl (2-(2,5-dioxo-2,5-dihydro-1H-pyrrole-1-yl)ethyl)carbamate

[C57]

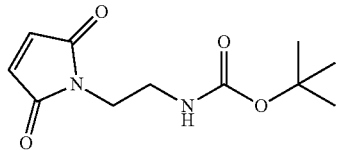

Maleic anhydride (600 mg) was suspended in ethanol (6.0 ml), and an ethanol (3.0 ml) solution of tert-butyl(2-aminoethyl) carbamate (1.03 g) and triethylamine (0.90 ml) was added under ice-water cooling. The reaction solution was stirred for 2 hours at room temperature, and the ethanol was distilled off under reduced pressure. The residue was dissolved in acetic anhydride (6.0 ml), sodium acetate (502 mg) was added, and the mixture was stirred for 1.5 hours at 70° C. This was separated by addition of ethyl acetate (25 ml) and water (10 ml). The organic layer was washed successively with saturated sodium bicarbonate water (10 ml, 3 times) and brine (10 ml) and dried with anhydrous sodium sulfate, and the solvent was distilled off under reduced pressure. The residue was purified by silica gel column chromatography (heptane to 50% ethyl acetate/heptane). The oily product was triturated with heptane (20 ml). The solid was collected by filtration, washed with heptane, and dried under reduced pressure to obtain the title compound (1.01 g) as a white solid.

NMR Data (CDCl$_3$) (δ: ppm): 6.71 (2H, s), 4.72 (1H, brs), 3.66 (2H, t, J=6 Hz), 3.33 (2H, q, J=6 Hz), 1.40 (9H, s)

<Step 2>

Synthesis of 1-(2-aminoethyl)-1H-pyrrole-2,5-dione hydrochloride

[C58]

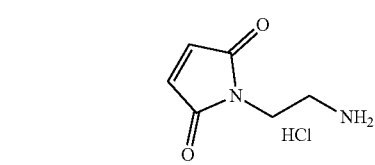

4N-hydrogen chloride ethyl acetate solution (5.0 ml) was added to the compound obtained in <Step 1> of (Example 1) (500 mg) and stirred for 1.5 hours at room temperature. After addition of ethyl acetate (5.0 ml), the precipitate was collected by filtration and washed with ethyl acetate. The resulting hygroscopic solid was suspended in ethyl acetate, the ethyl acetate was distilled off under reduced pressure, and the product was dried under reduced pressure to obtain the title compound (328 mg) as a white solid.

NMR Data (D$_2$O) (δ: ppm): 6.86 (2H, s), 3.80 (2H, t, J=6 Hz), 3.20 (2H, t, J=6 Hz)

\<Step 3\>

Synthesis of Alginic Acid (AL-EX-1) Having Introduced 2-(2,5-dioxo-2,5-dihydro-1H-pyrrole-1-yl)ethylamino Group

[C59]

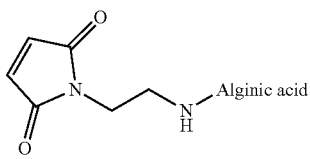
(AL-EX-1)

The compound (36 mg) obtained in \<Step 2\> of (Example 1), 4-(4,6-dimethoxy-1,3,5-triazin-2-yl)-4-methylmorpholinium chloride (84 mg) and 1-molar sodium bicarbonate water (252 µl) were added to 20 ml of an aqueous solution of sodium alginate (KIMICA Corporation, ALG-2) adjusted to 1 wt %, and stirred for 3 hours at 30° C. Sodium chloride (200 mg) was added, ethanol (40 ml) was added, and the mixture was stirred at room temperature for 30 minutes. The resulting precipitate was collected by filtration, washed with ethanol, and dried under reduced pressure to obtain the title compound (183 mg) as a white solid.

The introduction rate of the reactive group was 5.3 mol % (NMR integration ratio).

In terms of molecular weight, the substance was eluted broadly between 2,610,000 Da and 19,000 Da, and the weight-average molecular weight was calculated as 1,460,000 Da.

Example 2

Synthesis of Alginic Acid (AL-EX-2) Having Introduced 2-(2-(2,5-dioxo-2,5-dihydro-1H-pyrrole-1-yl)ethoxy)ethylamino Group

[C60]

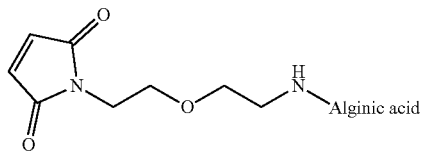
(AL-EX-2)

\<Step 1\>

Synthesis of tert-butyl (2-(2-(2,5-dioxo-2,5-dihydro-1H-pyrrole-1-yl)ethoxy)ethyl)carbamate

[C61]

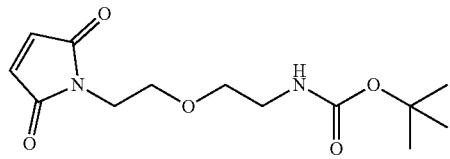

1H-pyrrole-2,5-dione (0.7 g), tert-butyl (2-(2-hydroxyethoxy)ethyl) carbamate (1.0 g) and triphenyl phosphine (1.4 g) were dissolved in tetrahydrofuran (20 ml). Diisopropyl azodicarboxylate (1.9 mol/L toluene solution, 2.8 ml) was dripped in under salt ice-water cooling, and the mixture was stirred for 30 minutes under ice-water cooling. This was stirred for 1 hour at room temperature and separated by addition of ethyl acetate (20 ml) and water (10 ml). The organic layer was washed with brine and dried with anhydrous sodium sulfate, and the solvent was distilled off under reduced pressure. The residue was purified by silica gel column chromatography (heptane to ethyl acetate), and dried under reduced pressure to obtain the title compound (0.5 g) as a light-yellow oily substance.

NMR Data (CDCl$_3$) (δ: ppm): 6.71 (2H, s), 4.87 (1H, brs), 3.72 (2H, t, J=6 Hz), 3.59 (2H, t, J=6 Hz), 3.49 (2H, t, J=5 Hz), 3.26 (2H, q, J=5 Hz), 1.44 (9H, s)

\<Step 2\>

Synthesis of 1-(2-(2-aminoethoxy)ethyl)-1H-pyrrole-2,5-dione trifluoroacetate Salt

[C62]

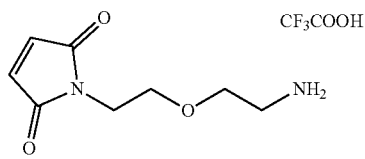

Trifluoroacetic acid (2.3 ml) was added under ice-water cooling to the compound (0.5 g) obtained in \<Step 1\> of (Example 2), and stirred for 1 hour at room temperature. Diisopropyl ether (11.3 ml) was added, the mixture was stirred for 30 minutes at room temperature, and the precipitated solid was collected by filtration and washed with diisopropyl ether. The resulting hygroscopic solid was suspended in diisopropyl ether, the solvent was distilled off, and the product was dried under reduced pressure to obtain the title compound (0.3 g) as a light-yellow solid.

NMR Data (DMSO-d$_6$) (δ: ppm): 7.73 (3H, brs), 7.04 (2H, s), 3.63 to 3.53 (6H, m), 2.98 to 2.89 (2H, m)

\<Step 3\>

Synthesis of Alginic Acid (AL-EX-2) Having Introduced 2-(2-(2,5-dioxo-2,5-dihydro-1H-pyrrole-1-yl)ethoxy) ethylamino Group

[C63]

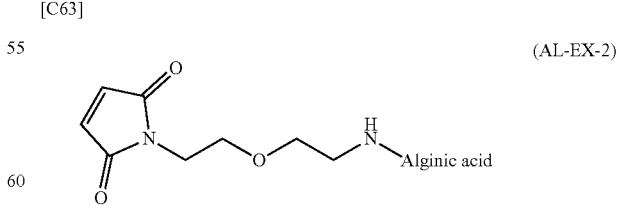
(AL-EX-2)

The title compound (183 mg) was obtained as a white solid by the same operations as in \<Step 3\> of (Example 1) using 20 ml of an aqueous solution of sodium alginate (KIMICA Corporation, ALG-2) adjusted to 1 wt % and the compound (60 mg) obtained in \<Step 2\> of (Example 2).

The introduction rate of the reactive group was 4.4 mol % (NMR integration ratio).

In terms of molecular weight, the substance was eluted broadly between 2,730,000 Da and 11,000 Da, and the weight-average molecular weight was calculated as 1,440,000 Da.

Example 3

Synthesis of Alginic Acid (AL-EX-3) Having Introduced 2-(2-(2-(2,5-dioxo-2,5-dihydro-1H-pyrrole-1-yl)ethoxy)ethoxy) ethylamino Group

[C64]

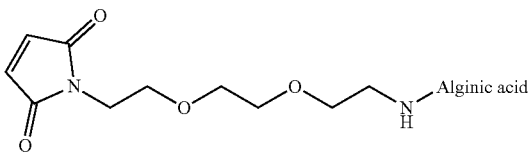

(AL-EX-3)

<Step 1>

Synthesis of tert-butyl (2-(2-(2-aminoethoxy)ethoxy)ethyl)carbamate

[C65]

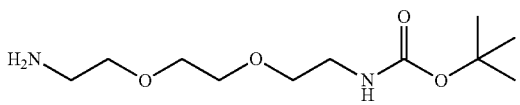

A methylene chloride (37.5 ml) solution of di-tert-butyl decarbonate (3.0 g) was dripped over the course of 4.75 hours under ice-water cooling into a methylene chloride (30.0 ml) solution of 2,2'-(ethane-1,2-diylbis(oxy))ethane-1-amine) (3.2 g) and triethylamine (11.5 ml), and stirred for 18.5 hours at room temperature. The reaction solution was concentrated under reduced pressure, methylene chloride (30 ml) was added to the residue, and insoluble matter was removed by filtration. The filtrate was washed successively with water (10 ml) and brine (10 ml) and dried with anhydrous sodium sulfate, and the solvent was distilled off under reduced pressure. The residue was dried under reduced pressure to obtain the title compound (2.7 g) as a colorless oily substance.

NMR Data (CDCl$_3$) (δ: ppm): 5.15 (1H, brs), 3.63 to 3.60 (4H, m), 3.55 (2H, t, J=5 Hz), 3.52 (2H, t, J=5 Hz), 3.32 (2H, q, J=5 Hz), 2.88 (2H, t, J=5 Hz), 1.45 (9H, s)

<Step 2>

Synthesis of tert-butyl (2-(2-(2-(2,5-dioxo-2,5-dihydro-1H-pyrrole-1-yl)ethoxy)ethoxy)ethyl)carbamate

[C66]

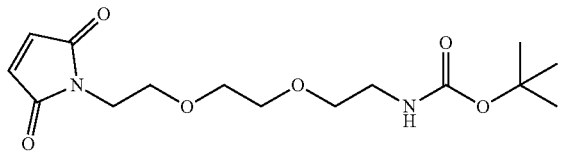

The compound (500 mg) obtained in <Step 1> of (Example 3) and maleic anhydride (217 mg) were suspended in ethanol (5.0 ml) and stirred for 30 minutes at room temperature. The ethanol was distilled off under reduced pressure, and the residue was purified by silica gel column chromatography (heptane to ethyl acetate) to obtain an amide (423 mg). Acetic anhydride (4.2 ml) was added to the resulting colorless oily substance and sodium acetate (100 mg), stirred for 1 hour at 40° C., and then stirred for 1 hour at 60° C., 1.5 hours at 80° C. and 2 hours at 100° C. The reaction solution was separated by addition of ethyl acetate (25 ml) and water (10 ml). The organic layer was washed successively with saturated sodium bicarbonate water (10 ml), water (10 ml) and brine (5 ml) and then dried with anhydrous sodium sulfate and concentrated under reduced pressure. The residue was purified by silica gel column chromatography (heptane to 80% ethyl acetate/heptane) to obtain the title compound (275 mg) as a colorless oily substance.

NMR Data (CDCl$_3$) (δ: ppm): 6.70 (2H, s), 5.01 (1H, brs), 3.76 to 3.72 (2H, m), 3.67 to 3.63 (2H, m), 3.61 to 3.58 (2H, m), 3.57 to 3.54 (2H, m), 3.50 (2H, t, J=5 Hz), 3.29 (2H, q, J=5 Hz), 1.45 (9H, s)

<Step 3>

Synthesis of 2-(2-(2-(2,5-dioxo-2,5-dihydro-1H-pyrrole-1-yl)ethoxy)ethoxy) ethylamine trifluoroacetate Salt

[C67]

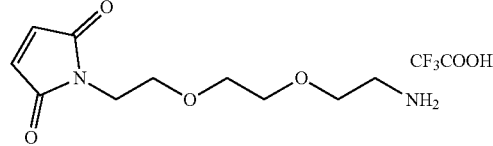

Trifluoroacetic acid (1.9 ml) was added under ice-water cooling to the compound (275 mg) obtained in <Step 2> of (Example 3), and stirred for 15 minutes at room temperature. The reaction solution was concentrated under reduced pressure, and the residue was purified by silica gel column chromatography (ethyl acetate to 30% methanol/ethyl acetate) to obtain the title compound (231 mg) as a colorless oily substance.

NMR Data (CDCl$_3$) (δ: ppm): 8.22 (3H, brs), 6.74 (2H, s), 3.75 to 3.71 (4H, m), 3.64 to 3.57 (6H, m), 3.19 (2H, t, J=5 Hz)

\<Step 4\>

Synthesis of Alginic Acid (AL-EX-3) Having Introduced 2-(2-(2-(2,5-dioxo-2,5-dihydro-1H-pyrrole-1-yl)ethoxy)ethoxy) ethylamino Group

[C68]

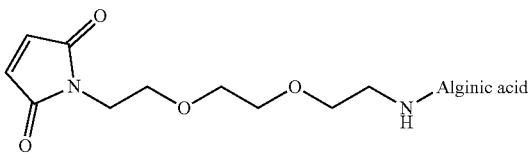

(AL-EX-3)

The title compound (145 mg) was obtained as a white solid by the same operations as in <Step 3> of (Example 1) using 20 ml of an aqueous solution of sodium alginate (KIMICA Corporation, ALG-2) adjusted to 1 wt % and 69 mg of the compound obtained in <Step 3> of (Example 3).

The introduction rate of the reactive group was 3.7 mol % (NMR integration ratio).

In terms of molecular weight, the substance was eluted broadly between 2,720,000 Da and 11,000 Da, and the weight-average molecular weight was calculated as 1,440,000 Da.

Example 4

Synthesis of Alginic Acid (AL-EX-4) Having Introduced S-(4-(2-aminoethyl)carbamoyl)benzyl) ethanethioate Group

[C69]

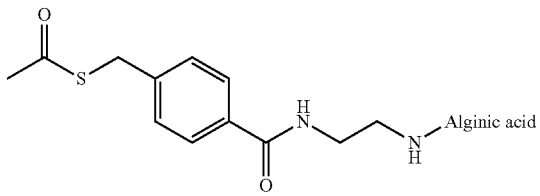

(AL-EX-4)

\<Step 1\>

Synthesis of tert-butyl (2-(4-(chloromethyl)benzamido)ethyl)carbamate

[C70]

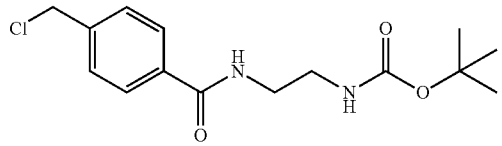

4-(chloromethyl)benzoyl chloride (2.0 g) was dissolved in tetrahydrofuran (10.0 ml), and a tetrahydrofuran (10.0 ml) solution of tert-butyl (2-aminoethyl)carbamate (1.7 g) and diisopropylethylamine (3.7 ml) was dripped in under ice-water cooling and stirred for 1.5 hours at room temperature. The reaction solution was separated by addition of ethyl acetate (30 ml) and water (10 ml). The organic layer was washed successively with semi-saturated sodium bicarbonate water (10 ml), water (10 ml) and brine (5 ml), dried with anhydrous sodium sulfate, and concentrated under reduced pressure. The residue was triturated with tert-butyl methyl ether, and the resulting solid was collected by filtration and washed with tert-butyl methyl ether to obtain the title compound (2.9 g) as a white solid.

NMR Data (CDCl$_3$) (δ: ppm): 7.81 (2H, d, J=8 Hz), 7.44 (2H, d, J=8 Hz), 7.24 (1H, brs), 4.96 (1H, brs), 4.60 (2H, s), 3.56 (2H, q, J=5 Hz), 3.45 to 3.38 (2H, m), 1.43 (9H, s)

\<Step 2\>

Synthesis of S-(4-((2-((tert-butoxycarbonyl)amino) ethyl)carbamoyl)benzyl) ethanethioate

[C71]

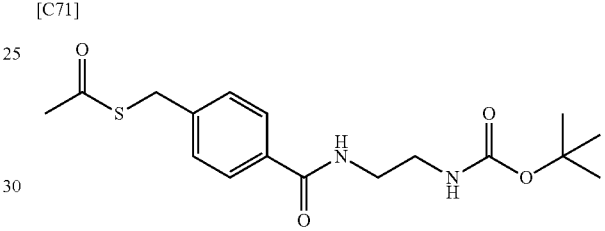

The compound (1.20 g) obtained in <Step 1> of (Example 4) was suspended in acetonitrile (24.0 ml). Potassium thioacetate (0.53 g) was added, and the mixture was stirred for 30 minutes at room temperature. The reaction solution was separated by addition of ethyl acetate (50 ml) and water (20 ml). The organic layer was washed successively with water (20 ml) and brine (10 ml), dried with anhydrous sodium sulfate, and concentrated under reduced pressure. The residue was triturated with tert-butyl methyl ether, and a solid was collected by filtration and washed with tert-butyl methyl ether. The resulting solid was dried under reduced pressure at 40° C. to obtain the title compound (1.27 g) as a white solid.

NMR Data (CDCl$_3$) (δ: ppm): 7.74 (2H, d, J=8 Hz), 7.33 (2H, d, J=8 Hz), 7.15 (1H, brs), 4.96 (1H, brs), 4.13 (2H, s), 3.54 (2H, q, J=5 Hz), 3.43 to 3.36 (2H, m), 2.36 (3H, s), 1.43 (9H, s)

\<Step 3\>

Synthesis of S-(4-(2-aminoethyl)carbamoyl)benzyl) ethanethioate hydrochloride

[C72]

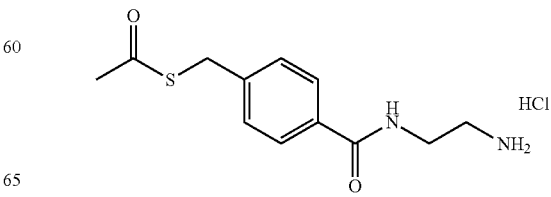

4N-hydrogen chloride/1,4-dioxane (4.2 ml) was added under ice-water cooling to the compound (0.60 g) obtained in <Step 2> of (Example 4) and stirred for 30 minutes at room temperature. 4N-hydrogen carbonate/1,4-dioxane (2.1 ml) was added, and the mixture was stirred for a further 30 minutes at room temperature. Diisopropyl ether (12.6 ml) was added to the reaction solution, and the resulting precipitate was collected by filtration, washed with diisopropyl ether, and dried under reduced pressure to obtain the title compound (0.46 g) as a white solid.

NMR Data (DMSO-$d_6$) (δ: ppm): 8.65 (1H, t, J=6 Hz), 7.85 (3H, brs), 7.82 (2H, d, J=8 Hz), 7.38 (2H, d, J=8 Hz), 4.16 (2H, s), 3.49 (2H, q, J=6 Hz), 2.97 (2H, t, J=6 Hz), 2.36 (3H, s)

<Step 4>

Synthesis of Alginic Acid (AL-EX-4) Having Introduced S-(4-(2-aminoethyl)carbamoyl)benzyl) ethanethioate Group

[C73]

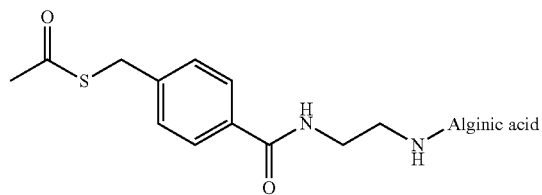

(AL-EX-4)

The title compound (189 mg) was obtained as a white solid by the same operations as in <Step 3> of (Example 1) using 20 ml of an aqueous solution of sodium alginate (KIMICA Corporation, ALG-2) adjusted to 1 wt % and 58 mg of the compound obtained in <Step 3> of (Example 4).

The introduction rate of the reactive group was 5.6 mol % (NMR integration ratio).

In terms of molecular weight, the substance was eluted broadly between 2,770,000 Da and 14,000 Da, and the weight-average molecular weight was calculated as 1,420,000 Da.

Example 5

Synthesis of Alginic Acid (AL-EX-5) Having Introduced S-(4-(3-((3-aminopropyl)amino)-3-oxopropyl)benzyl) ethanethioate Group

[C74]

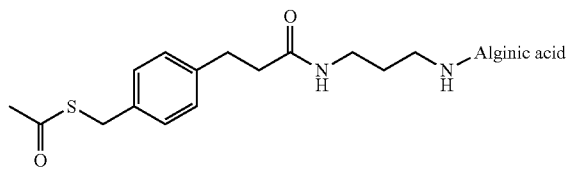

(AL-EX-5)

<Step 1>

Synthesis of methyl 4-(3-((3-((tert-butoxycarbonyl)amino)propyl)amino)-3-oxopropyl)benzoate

[C75]

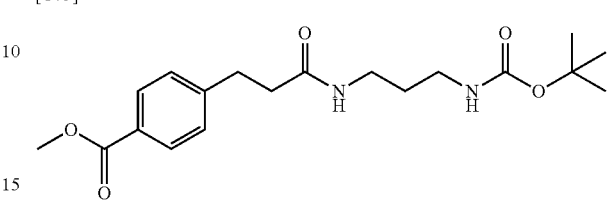

3-(4-(methoxycarbonyl)phenyl)propanoic acid (1.15 g) and tert-butyl (3-aminopropyl) carbamate (0.96 g) were dissolved in methanol (11.5 ml). 4-(4,6-dimethoxy-1,3,5-triazin-2-yl)-4-methylmorpholinium chloride (2.14 g) was added, and the mixture was stirred for 2 hours at room temperature and 1 hour at 40° C. The reaction solution was separated by addition of ethyl acetate (20 ml) and water (20 ml), and the water layer was extracted with ethyl acetate (10 ml). The organic layers were combined, washed successively with semi-saturated sodium bicarbonate water (10 ml), water (10 ml) and brine (5 ml) and dried with anhydrous sodium sulfate, and the solvent was distilled off under reduced pressure. The residue was purified by silica gel column chromatography (10% ethyl acetate/heptane to ethyl acetate) to obtain the title compound (0.76 g) as a colorless oily sub stance.

NMR Data (CDCl$_3$) (δ: ppm): 7.95 (2H, d, J=8 Hz), 7.28 (2H, d, J=8 Hz), 6.19 (1H, brs), 4.79 (1H, brs), 3.90 (3H, s), 3.25 (2H, q, J=6 Hz), 3.08 to 3.01 (4H, m), 2.51 (2H, t, J=8 Hz), 1.57 to 1.49 (2H, m), 1.43 (9H, s)

<Step 2>

Synthesis of tert-butyl (3-(3-(4-(hydroxymethyl)phenyl)propanamido)propyl)carbamate

[C76]

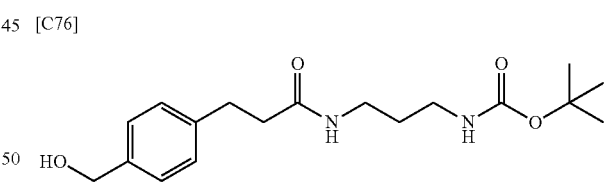

The compound (560 mg) obtained in <Step 1> of (Example 5) was dissolved in tetrahydrofuran (11.2 ml). Lithium aluminum hydride (146 mg) was added over the course of 5 minutes, and the mixture was stirred for 1 hour at room temperature. Saturated sodium sulfate aqueous solution (50 drops) was added under ice-water cooling, and the mixture was stirred for 1 hour at the same temperature. Precipitated insoluble matter was removed by filtration, and the product was washed with tetrahydrofuran. The filtrate was concentrated under reduced pressure to obtain the title compound (569 mg) as a colorless oily substance.

NMR Data (CDCl$_3$) (δ: ppm): 7.28 (2H, d, J=8 Hz), 7.20 (2H, d, J=8 Hz), 5.95 (1H, brs), 4.79 (1H, brs), 4.65 (2H, s), 3.23 (2H, q, J=6 Hz), 2.99 to 2.92 (4H, m), 2.48 (2H, t, J=7 Hz), 1.54 to 1.47 (2H, m), 1.44 (9H, s)

<Step 3>

Synthesis of 4-(3-((3-((tert-butoxycarbonyl)amino)propyl)amino)-3-oxopropyl)benzyl-4-methylbenzenesulfonate

[C77]

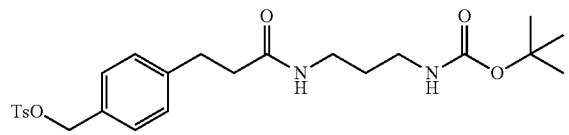

The compound (400 mg) obtained in <Step 2> of (Example 5) was dissolved in tetrahydrofuran (8.0 ml). p-Toluenesulfonyl chloride (272 mg), N,N-dimethyl-4-aminopyridine (15 mg) and triethylamine (0.33 ml) were added, and stirred for 6 hours at 70° C. The reaction solution was separated by addition of ethyl acetate (25 ml) and water (10 ml), and the water layer was extracted with ethyl acetate (5 ml). The organic layers were combined, washed successively with semi-saturated sodium bicarbonate water (10 ml), water (10 ml) and brine (5 ml), dried with anhydrous sodium sulfate, and concentrated under reduced pressure. The residue was triturated with tert-butyl methyl ether/heptane, and the resulting solid was collected by filtration and washed with heptane to obtain the title compound (224 mg) as a light beige solid.

NMR Data (CDCl$_3$) (δ: ppm): 7.30 (2H, d, J=8 Hz), 7.20 (2H, d, J=8 Hz), 6.13 (1H, brs), 4.81 (1H, brs), 4.56 (2H, s), 3.28 to 3.21 (2H, m), 3.04 (2H, q, J=6 Hz), 2.97 (2H, t, J=8 Hz), 2.48 (2H, t, J=8 Hz), 1.56 to 1.47 (2H, m), 1.43 (9H, s)

<Step 4>

Synthesis of S-(4-(3-((3-((tert-butoxycarbonyl)amino)propyl)amino)-3-oxopropyl)benzyl)ethanthioate

[C78]

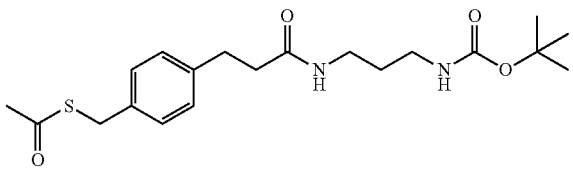

The compound (224 mg) obtained in <Step 3> of (Example 5) was suspended in acetonitrile (4.5 ml). Potassium thioacetate (87 mg) was added, and the mixture was stirred for 30 minutes at room temperature. The reaction solution was separated by addition of ethyl acetate (20 ml) and water (10 ml). The organic layer was washed successively with water (10 ml) and brine (5 ml), dried with anhydrous sodium sulfate, and concentrated under reduced pressure. The residue was purified by silica gel column chromatography (10% ethyl acetate/heptane to ethyl acetate) to obtain the title compound (189 mg) as a white solid.

NMR Data (CDCl$_3$) (δ: ppm): 7.19 (2H, d, J=8 Hz), 7.13 (2H, d, J=8 Hz), 6.07 (1H, brs), 4.82 (1H, brs), 4.08 (2H, s), 3.25 (2H, q, J=6 Hz), 3.04 (2H, q, J=6 Hz), 2.94 (2H, t, J=8 Hz), 2.46 (2H, t, J=8 Hz), 2.34 (3H, s), 1.56 to 1.49 (2H, m), 1.43 (9H, s)

<Step 5>

Synthesis of S-(4-(3-((-aminopropyl)amino)-3-oxopropyl)benzyl) ethanethioate hydrochloride

[C79]

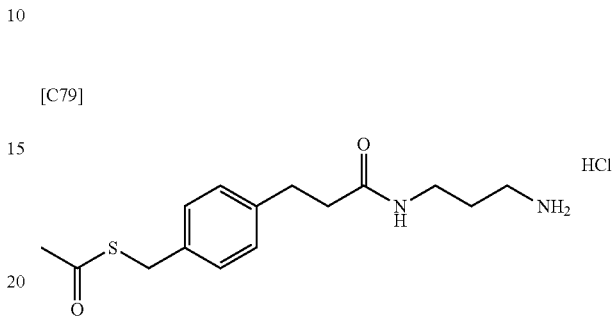

The title compound (140 mg) was obtained as a white solid by the same operations as in <Step 3> of (Example 4) using the compound (189 mg) obtained in <Step 4> of (Example 5).

NMR Data (DMSO-d$_6$) (δ: ppm): 8.03 (1H, t, J=6 Hz), 7.79 (3H, brs), 7.18 (2H, d, J=8 Hz), 7.12 (2H, d, J=8 Hz), 4.07 (2H, s), 3.09 (2H, q, J=6 Hz), 2.77 (2H, t, J=8 Hz), 2.75 to 2.66 (2H, m), 2.38 to 2.33 (2H, m), 2.34 (3H, s), 1.68 to 1.60 (2H, m)

<Step 6>

Synthesis of Alginic Acid (AL-EX-5) Having Introduced S-(4-(3-((3-aminopropyl)amino)-3-oxopropyl)benzyl) ethanethioate Group

[80]

(AL-EX-5)

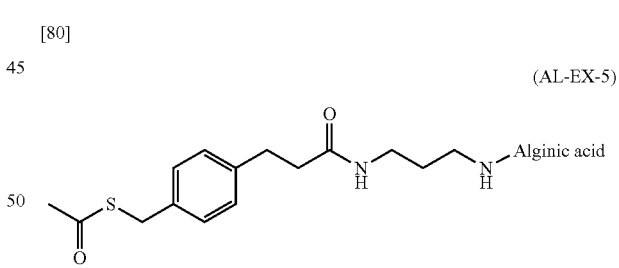

The title compound (189 mg) was obtained as a white solid by the same operations as in <Step 3> of (Example 1) using 20 ml of an aqueous solution of sodium alginate (KIMICA Corporation, ALG-2) adjusted to 1 wt % and the compound (67 mg) obtained in <Step 5> of (Example 5).

The introduction rate of the reactive group was 4.2 mol % (NMR integration ratio).

In terms of molecular weight, the substance was eluted broadly between 2,610,000 Da and 21,000 Da, and the weight-average molecular weight was calculated as 1,420,000 Da.

Example 7-1

Preparing Aqueous Solution of Alginic Acid (AL-EX-7-1) Having Introduced 2-(N-(4-(mercaptomethyl)benzamido)) ethylamino Group

[C81]

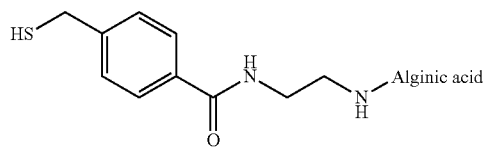
(AL-EX-7-1)

The compound (160 mg) obtained in <Step 4> of (Example 4) was dissolved in water (8.0 ml), and 1N-sodium hydroxide aqueous solution (112 μl) was added and stirred for 2 hours at 25° C. to obtain a 2 wt % solution of the title compound. Because ethanol precipitation treatment causes gelling, the solution was tested as is. Part was treated with ethanol, and loss of acetyl groups was confirmed by NMR.

Example 8

Synthesis of Alginic Acid (AL-EX-8) Having Introduced 2-amino-N-(2-(2,5-dioxo-2,5-dihydro-1H-pyrrole-1-yl)ethyl) acetamide Group

[C82]

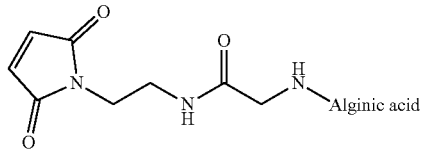
(AL-EX-8)

<Step 1>

Synthesis of tert-butyl (2-((2-(2,5-dioxo-2,5-dihydro-1H-pyrrole-1-yl)ethyl)amino)-2-oxoethyl) carbamate

[C83]

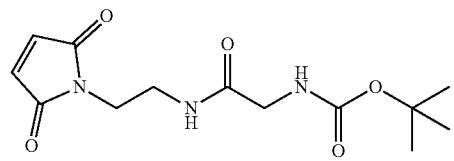

1-molar sodium bicarbonate water (578.5 μl) was added at room temperature to a mixture of commercial 1-(2-aminoethyl)-1H-pyrrole-2,5-dione hydrochloride [CAS No. 134272-64-3] (92.43 mg) and water (750 μl). A tetrahydrofuran (1,500 μl) solution of commercial 2,5-dioxopyrrolidine-1-yl(tert-butoxycarbonyl) glycinate [CAS No. 3392-07-2] (150 mg) was added to this mixture at room temperature, and the mixture was stirred for 30 minutes at that temperature. Upon completion of the reaction, this was separated by addition of ethyl acetate (10 ml) and water (5 ml). The organic layer was dried with anhydrous sodium sulfate, filtered, and then concentrated under reduced pressure. The coarse product was purified by silica gel column chromatography (25% ethyl acetate/heptane to 100% ethyl acetate, ethyl acetate to 60% methanol/ethyl acetate) to obtain the title compound (74 mg) as a colorless oily substance.

NMR Data (CDCl$_3$) (δ: ppm): 6.72 (2H, s), 6.59 (1H, br s), 5.18 (1H, br s), 3.74 (2H, d, J=6 Hz), 3.72 to 3.68 (2H, m), 3.50 to 3.46 (2H, m), 1.45 (9H, s)

<Step 2>

Synthesis of 2-amino-N-(2-(2,5-dioxo-2,5-dihydro-1H-pyrrole-1-yl)ethyl)acetamide trifluoroacetate Salt

[C84]

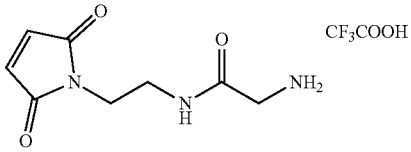

Trifluoroacetic acid (0.52 ml) was added under ice cooling and stirring to a mixture of the compound (0.074 g) obtained in <Step 1> of (Example 8) and dichloromethane (0.22 ml), and stirred for 2 hours at room temperature. Upon completion of the reaction, the reaction solution was concentrated, and diisopropyl ether (20 ml) was added. Because a rubbery compound was formed, the mixture was concentrated under reduced pressure and dried to obtain the title coarse compound (0.097 g) as a light-yellow rubbery compound.

NMR Data (DMSO-d$_6$) (δ: ppm): 8.45 (1H, t, J=6 Hz), 8.00 (3H, br s), 7.03 (2H, s), 3.48 (2H, t, J=6 Hz), 3.43 (2H, q, J=6 Hz), 3.29 (2H, q, J=6 Hz)

<Step 3>

Synthesis of Alginic Acid (AL-EX-8) Having Introduced 2-amino-N-(2-(2,5-dioxo-2,5-dihydro-1H-pyrrole-1-yl)ethyl) acetamide Group

[C85]

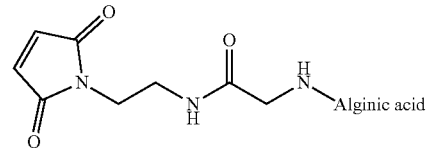
(AL-EX-8)

4-(4,6-dimethoxy-1,3,5-triazine-2-yl)-4-methylmorpholinium chloride (68.6 mg) and 1-molar sodium bicarbonate water (68.6 μl) were added at room temperature to 29.7 ml of an aqueous solution of sodium alginate (KIMICA Corporation, ALG-2) adjusted to 1 wt %. A mixture of the compound (21.4 mg) obtained in <Step 2> of (Example 8), water (1 ml) and ethanol (1 ml) was then added gradually at the same temperature, and stirred for 4 hours at 40° C. Sodium chloride (300 mg) was added, ethanol (59.3 ml) was added, and the mixture was stirred for 30 minutes at room temperature. The resulting precipitate was collected by filtration, washed with ethanol, and dried under reduced pressure to obtain the title compound (221.3 mg) as a white flocculent compound.

The introduction rate of the reactive group was 4.8 mol % (NMR integration ratio).

In terms of molecular weight, the substance was eluted broadly between 2,730,000 Da and 2,000 Da, and the weight-average molecular weight was calculated as 1,360,000 Da.

Example 9

Synthesis of Alginic Acid (AL-EX-9) Having Introduced (S)-2-amino-N-(2-(2,5-dioxo-2,5-dihydro-1H-pyrrole-1-yl)ethyl)-3-phenylpropanamide Group

[C86]

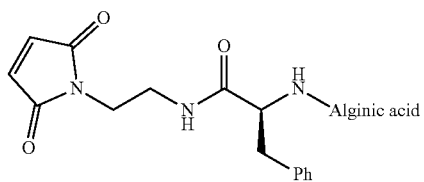

(AL-EX-9)

<Step 1>

Synthesis of tert-butyl (S)-(1-((2-(2,5-dioxo-2,5-dihydro-1H-pyrrole-1-yl)ethyl)amino)-1-oxo-3-phenylpropane-2-yl)carbamate

[C87]

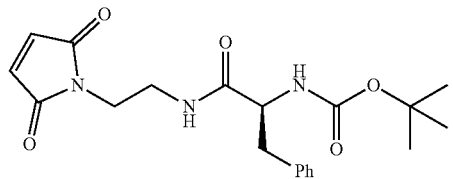

Triethylamine (78.9 µl) was added under ice cooling and stirring to a mixture of commercial 1-(2-aminoethyl)-1H-pyrrole-2,5-dione hydrochloride [CAS No. 134272-64-3] (100 mg), commercial (tert-butoxycarbonyl)-L-phenylalanine [CAS No. 13734-34-4] (150.23 mg) and dichloromethane (1 ml). N,N'-dicyclohexylcarbodiimide (116.8 mg) was added to this mixture at the same temperature, and stirred for 30 minutes at room temperature. Upon completion of the reaction, this was diluted with ethyl acetate (20 ml), and the suspension was filtered. The coarse product was purified by silica gel column chromatography (12% ethyl acetate/heptane to 100% ethyl acetate) to obtain the title compound (108 mg) as a white amorphous substance.

NMR Data (CDCl$_3$) (δ: ppm): 7.30 to 7.27 (2H, m), 7.23 to 7.17 (3H, m), 6.68 (2H, s), 6.19 (1H, br s), 4.91 (1H, br s), 4.30 to 4.26 (1H, m), 3.66 to 3.53 (2H, m), 3.50 to 3.41 (1H, m), 3.36 to 3.30 (1H, m), 3.08 to 2.98 (2H, m), 1.39 (9H, s)

<Step 2>

Synthesis of (S)-2-amino-N-(2-(2,5-dioxo-2,5-dihydro-1H-pyrrole-1-yl)ethyl)-3-phenylpropanamide trifluoroacetate Salt

[C88]

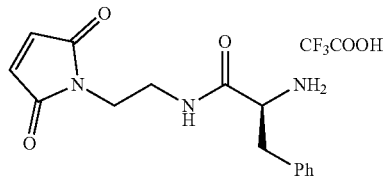

Trifluoroacetic acid (0.7 ml) was added under ice cooling and stirring to a mixture of the compound (0.1 g) obtained in <Step 1> of (Example 9) and dichloromethane (1.3 ml) and stirred for 30 minutes at room temperature. Upon completion of the reaction the reaction solution was concentrated under reduced pressure, and diisopropyl ether (20 ml) was added. The suspension was filtered to obtain the title compound (0.12 g) as a white solid.

NMR Data (DMSO-d$_6$) (δ: ppm): 8.57 (1H, t, J=6 Hz), 8.07 (3H, br s), 7.36 to 7.33 (2H, m), 7.30 to 7.22 (3H, m), 7.05 (2H, s), 3.85 (1H, dd, J=8.6 Hz), 3.45 to 3.40 (3H, m), 3.18 to 3.13 (1H, m), 3.01 (1H, dd, J=14, 5 Hz), 2.83 (1H, dd, J=14, 9 Hz)

<Step 3>

Synthesis of Alginic Acid (AL-EX-9) Having Introduced (S)-2-amino-N-(2-(2,5-dioxo-2,5-dihydro-1H-pyrrole-1-yl)ethyl)-3-phenylpropanamide Group

[C89]

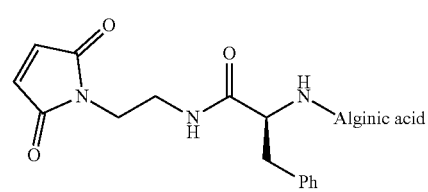

(AL-EX-9)

The title compound (264.8 mg) was obtained as a white flocculent compound by the same operations as in <Step 3> of (Example 8) using an aqueous solution of sodium alginate (KIMICA Corporation, ALG-2) adjusted to 1 wt % and the compound (27.5 mg) obtained in <Step 2> of (Example 9).

The introduction rate of the reactive group was 6.0 mol % (NMR integration ratio).

In terms of molecular weight, the substance was eluted broadly between 2,770,000 Da and 6,000 Da, and the weight-average molecular weight was calculated as 1,460,000 Da.

Example 10

Synthesis of Alginic Acid (AL-EX-10) Having Introduced (S)-2-(2-aminoacetoamido)-N-(2-(2,5-dioxo-2,5-dihydro-1H-pyrrole-1-yl)ethyl)-3-phenyl-propanamide Group

[C90]

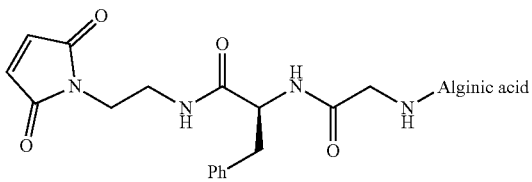

(AL-EX-10)

<Step 1>

Synthesis of (Tert-Butoxycarbonyl) Glycyl-L-Phenylalanine

[C91]

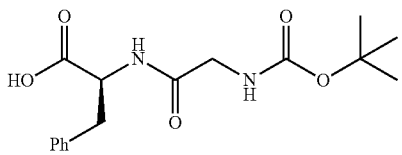

1-molar sodium bicarbonate water (0.73 ml) was added at room temperature to a mixture of commercial L-phenylalanine [CAS No. 63-91-2] (0.12 g) and water (1 ml). A tetrahydrofuran (4 ml) solution of commercial 2,5-dioxopyrrolidine-1-yl(tert-butoxycarbonyl) glycinate [CAS No. 3392-07-2] (0.2 g) was added to this mixture at room temperature and stirred at that temperature. After 1 hour and 30 minutes, more 2,5-dioxopyrrolidine-1-yl(tert-butoxycarbonyl) glycinate (0.02 g) was added, and the mixture was stirred at room temperature for 30 minutes. Upon completion of the reaction, ethyl acetate (10 ml) and 1-N hydrochloric acid (3 ml) were added to separate the solution. The organic layer was washed successively with water (5 ml) and brine (5 ml), dried with anhydrous sodium sulfate, filtered, and then concentrated under reduced pressure. The coarse product was purified by silica gel column chromatography (25% ethyl acetate/heptane to 100% ethyl acetate, ethyl acetate to 20% methanol/ethyl acetate) to obtain the title compound (0.21 g) as a white amorphous substance.

NMR Data (CDCl$_3$) (δ: ppm): 7.31 to 7.20 (3H, br m), 7.16 to 7.13 (2H, m), 6.65 (1H, br s), 5.26 (1H, br s), 4.86 (1H, br s), 3.88 (1H, dd, J=17, 7 Hz), 3.68 (1H, dd, J=17, 6 Hz), 3.24 to 3.05 (2H, m), 1.44 (9H, s)

<Step 2>

Synthesis of tert-butyl (S)-(2-((1-((2-(2,5-dioxo-2,5-dihydro-1H-pyrrole-1-yl)ethyl)amino)-1-oxo-3-phenylpropane-2-yl)amino)-2-oxoethyl)carbamate

[C92]

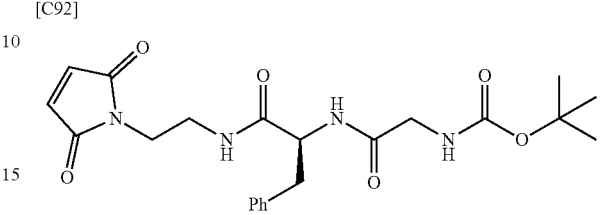

Triethylamine (90 μl) was added under ice cooling and stirring to a mixture of commercial 1-(2-aminoethyl)-1H-pyrrole-2,5-dione hydrochloride [CAS No. 134272-64-3] (114 mg), the compound (208 mg) obtained in <Step 1> of (Example 10) and dichloromethane (2,080 μl). N,N'-dicyclohexylcarbodiimide (133.1 mg) was added at the same temperature to this mixture, which was then stirred for 1 hour and 30 minutes at room temperature. Upon completion of the reaction this was diluted with ethyl acetate (20 ml), and the suspension was filtered. The coarse product was purified by silica gel column chromatography (25% ethyl acetate/heptane to 100% ethyl acetate, ethyl acetate to 20% methanol/ethyl acetate). The collected fraction was concentrated under reduced pressure and dissolved in tert-butyl methyl ether (20 ml). This solution was washed successively with saturated sodium bicarbonate water (5 ml), water (5 ml, twice) and brine (5 ml), and dried with anhydrous sodium sulfate. The organic layer was concentrated under reduced pressure to obtain the title compound (220 mg) as a white amorphous substance.

NMR Data (CDCl$_3$) (δ: ppm): 7.29 to 7.27 (2H, m), 7.24 to 7.16 (3H, m), 6.67 (2H, s), 6.47 (1H, br s), 6.40 (1H, d, J=8 Hz), 5.14 (1H, br s), 4.66 to 4.60 (1H, m), 3.85 to 3.45 (5H, m), 3.29 to 3.23 (1H, m), 3.09 (2H, d, J=7 Hz), 1.44 (9H, s)

<Step 3>

Synthesis of (S)-2-(2-aminoacetamido)-N-(2-(2,5-dioxo-2,5-dihydro-1H-pyrrole-1-yl)ethyl)3-phenyl-propanamide trifluoroacetate Salt

[C93]

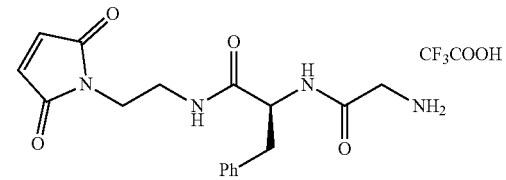

The title compound (0.25 g) was obtained as a white solid by the same operations as in <Step 2> of (Example 9) using the compound (0.22 g) obtained in <Step 2> of (Example 10).

NMR Data (DMSO-d$_6$) (δ: ppm): 8.67 (1H, d, J=8 Hz), 8.33 (1H, t, J=6 Hz), 7.89 (3H, br s), 7.29 to 7.24 (2H, m), 7.23 to 7.17 (3H, m), 7.03 (2H, s), 4.46 to 4.40 (1H, m), 3.48 to 3.41 (3H, m), 3.38 to 3.28 (2H, m), 3.17 to 3.11 (1H, m), 2.94 (1H, dd, J=14, 4 Hz), 2.67 (1H, dd, J=14, 10 Hz)
<Step 4>

Synthesis of Alginic Acid (AL-EX-10) Having Introduced (S)-2-(2-aminoacetoamido)-N-(2-(2,5-dioxo-2,5-dihydro-1H-pyrrole-1-yl)ethyl)-3-phenyl-propanamide Group

[C94]

(AL-EX-10)

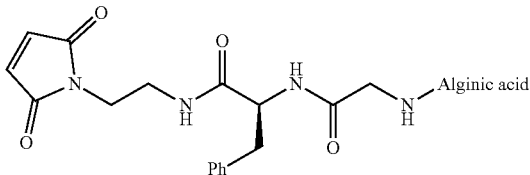

The title compound (485 mg) was obtained as a white flocculent compound by the same operations as in <Step 3> of (Example 8) using an aqueous solution of sodium alginate (KIMICA Corporation, ALG-2) adjusted to 1 wt % and the compound (52.4 mg) obtained in <Step 3> of (Example 10).

The introduction rate of the reactive group was 5.3 mol % (NMR integration ratio).

In terms of molecular weight, the substance was eluted broadly between 2,870,000 Da and 20,000 Da, and the weight-average molecular weight was calculated as 1,430,000 Da.

<Measuring Introduction Rate of Reactive Group>

The introduction rate of the reactive group is a percentage value representing the number of introduced reactive groups relative to the number of uronic acid monosaccharide units that are repeating units of the alginate. The amount of alginic acid necessary for calculating the introduction rate is measured by the carbazole-sulfuric acid method using a calibration curve, and the quantity of reactive groups is measured by the absorbance measurement method using a calibration curve.

<Measuring Molecular Weight>

The alginic acid solid with introduced crosslinking group obtained in each example was weighed, a 10 mmol/L phosphoric acid buffer (pH 7.4) containing 0.15 mol/L NaCl was added, and the mixture was stirred to dissolve for at least 1 hour at room temperature to prepare an 0.2% solution. This solution was passed through a polyether sulfone Minisart High Flow filter with a pore size of 0.45 microns (Sartorius) to exclude insoluble matter, after which 200 µl was supplied to a Superose 6 Increase 10/300 GL column (GE Health Care Sciences) and subjected to gel filtration. Gel filtration was performed at room temperature at a flow rate of 0.8 ml/min using an AKTA Explorer 10S as the chromatograph unit and 10 mmol/L phosphoric acid buffer (pH 7.4) containing 0.15 mol/L NaCl as the development solvent. The chromatogram for each sample was prepared by monitoring absorbance at 220 nm or 240 nm. In a different method, absorbance at 215 nm was monitored. Peak analysis of the resulting chromatograms was performed using Unicorn 5.31 software (GE Health Care Sciences).

The molecular weights of the alginic acids with introduced crosslinking groups were determined by performing gel filtration under the same conditions using blue dextran (molecular weight 2,000,000 Da, SIGMA), thyroglobulin (molecular weight 669,000 Da, GE Health Care Sciences), ferritin (molecular weight 440,000 Da, GE Health Care Sciences), aldolase (molecular weight 158,000 Da, GE Health Care Sciences), conalbumin (molecular weight 75,000 Da, GE Health Care Sciences), ovalbumin (molecular weight 44,000 Da, GE health Care Sciences), ribonuclease A (molecular weight 13,700 Da, GE Health Care Sciences) and aprotinin (molecular weight 6,500 Da, GE Health Care Sciences) as standard substances, and preparing a calibration curve from the liquid volumes and molecular weights of the absorption peaks of each component at 280 nm. Two calibration curves were prepared, one for blue dextran to ferritin and one for ferritin to aprotinin. Using these calibration curves, the molecular weights (Mi) at the elution times i in the chromatogram obtained above were calculated. Next, the absorbance values at the elution times i were read and given as Hi, and the weight-average molecular weights (Mw) were then determined by the following formula from these data.

$$Mw = \frac{\sum_{i=1}^{\infty}(H^{i \times Mi})}{\sum_{i=1}^{\infty} Hi}$$ [Math. 1]

The molecular weight of the alginic acid before crosslinking group introduction was determined as follows. That is, each alginic acid was weighed in consideration of drying loss, and ultrapure water was added to prepare a 1% aqueous solution. This was then diluted to obtain an alginic acid concentration of 0.2% in a 10 mmol/L phosphoric acid buffer (pH 7.4) containing 0.15 mol/L NaCl. Insoluble matter was removed with a hydrophilic PVDF Mylex GV33 filter (Merck-Millipore Co.) with a pore size of 0.22 microns, and 200 µl was supplied to gel filtration and filtered under the same conditions as the alginic acids with introduced crosslinking groups. Detection was performed with a differential refractometer. As a different method, insoluble matter was removed with a polyether sulfone Minisart High Flow filter (Sartorius) having a pore size of 0.45 microns.

The weight-average molecular weight of the alginic acid before crosslinking group introduction was determined by the same methods used to calculate the molecular weight of the alginic acids with introduced crosslinking groups. Hi was calculated from the differential refractometer data.

In terms of molecular weight, the alginic acid before crosslinking group introduction (ALG-2) used in Examples 1 to 5 and Example 7-1 exhibited broad elution between 2,600,000 Da and 145,000 Da, and the weight-average molecular weight was calculated as 1,460,000 Da.

In terms of molecular weight, the alginic acid before crosslinking group introduction (ALG-2) used in Examples 8 to 10 exhibited broad elution between 9,600 Da and 2,510,000 Da, and the weight-average molecular weight was calculated as 1,380,000 Da.

<Measuring Gel Stability>

The alginic acid derivative (AL-EX-2) obtained in <Step 3> of (Example 2) and the alginic acid derivative (AL-EX-3) obtained in <Step 4> of (Example 3) were each dissolved in water to a concentration of 1% to obtain an aqueous alginic acid solution (2) and an aqueous alginic acid solution (3). An equal amount of phosphate buffered saline (PBS) was also added to the 2 wt % alginic acid derivative (AL-EX-7-1) solution obtained in (Example 7-1) to obtain an aqueous alginic acid solution (7-1) with a concentration of 1 wt %.

The aqueous alginic acid solution (2) and aqueous alginic acid solution (7-1) were mixed in equal amounts, this mixed aqueous solution was placed in a syringe equipped with an 18-gauge needle, this syringe was attached to a syringe pump set to a flow rate of 1 ml/minute, and the solution was dripped for 30 seconds into a 30 mmol/L calcium chloride solution, which was then stirred for 5 minutes to obtain an alginic acid gel. This gel was washed once with 10 ml of PBS, and then left for 10 minutes at 37° C. to perform chemical crosslinking and obtain a chemically crosslinked alginic acid gel. 20 ml of PBS was added to this gel and shaken at 37° C., the aqueous solution was collected over time, and the gel was replenished with PBS in the same amount as the collected amount. Upon completion of testing, 2 µl of alginate lyase (Nippon Gene, 319-08261) was added to the test solution, which was then shaken for 1 hour at 37° C. to completely collapse the gel, and the aqueous solution was collected. The alginic acid concentration in the collected aqueous solution was measured by the carbazole-sulfuric acid method, the alginic acid concentration in the aqueous solution at each point in time was corrected by the alginic acid concentration of the previously collected solution, the resulting value was divided by the total alginic acid concentration calculated from the alginic acid concentration at all time points and the alginic acid concentration after completion of testing, and the resulting value represented as a percentage was given as a gel collapse rate and used as an indicator of gel stability. Alginic acid gels obtained by the above methods using the aqueous alginic acid solution (3) and aqueous alginic acid solution (7-1) were also measured for gel stability.

The results are shown in FIG. 1.

While the alginic acid gel prepared from the alginic acid (ALG-2) used as a control dissolved almost completely within 8 hours, the crosslinked alginic acid structures obtained by crosslinking alginic acid derivatives with introduced crosslinking groups of the examples (crosslinked alginic acid structure obtained by crosslinking alginic acid derivative (AL-EX-2)/alginic acid derivative (AL-EX-7-1) and alginic acid structure obtained by crosslinking alginic acid derivative (AL-EX-3)/alginic acid derivative (AL-EX-7-1)) all had improved stability.

<Measuring Gel Stability (2)>

The alginic acid derivative (AL-EX-8) obtained in Example 8, the alginic acid derivative (AL-EX-9) obtained in Example 9 and the alginic acid derivative (AL-EX-10) obtained in Example 10 were each dissolved in water to a concentration of 0.5% to obtain an aqueous alginic acid solution (8), aqueous alginic acid solution (9) and aqueous alginic acid solution (10). Three times the volume of phosphate buffered saline (PBS) was also added to a 2% alginic acid derivative with introduced crosslinking group (AL-EX-7-1-2) obtained by the same methods as Example 7-1 (introduction rate (NMR integration ratio)=5.1 mol %) to a concentration of 0.5% to obtain an aqueous alginic acid solution (7-1-2).

The aqueous alginic acid solution (8), aqueous alginic acid solution (9) and aqueous alginic acid solution (10) (250 µl) were each mixed with an equal amount of the aqueous alginic acid solution (7-1-2), and 40 ml of a 30 mmol/L calcium chloride solution was added to each mixture, which was then stirred for 5 minutes to obtain an alginic acid gel. This gel was washed once with 10 ml of PBS to obtain a chemically crosslinked alginic acid gel. 19.5 ml of PBS was added to this gel and shaken at 37° C., the aqueous solution was collected over time, and the gel was replenished with PBS in the same amount as the collected amount. Upon completion of testing 10 µl of alginate lyase (Nippon Gene, 319-08261) was added to the test solution, which was then shaken overnight at 37° C. to completely collapse the gel, and the aqueous solution was collected. The alginic acid concentration in the collected aqueous solution was measured by the carbazole-sulfuric acid method, the alginic acid concentration in the aqueous solution at each point in time was corrected by the alginic acid concentration of the previously collected solution, the resulting value was divided by the total alginic acid concentration calculated from the alginic acid concentration at all time points and the alginic acid concentration after completion of testing, and the resulting value represented as a percentage was given as the gel collapse rate and used as an indicator of gel stability.

The results are shown in FIG. 3.

The crosslinked alginic acid structure obtained by crosslinking the alginic acid derivative (AL-EX-9)/alginic acid derivative (AL-EX-7-1-2) had a collapse rate of about 39% after 96 hours, the crosslinked alginic acid structure obtained by crosslinking the alginic acid derivative (AL-EX-8)/(AL-EX-7-1-2) had a collapse rate of about 40% after 96 hours and the crosslinked alginic acid structure obtained by crosslinking the alginic acid derivative (AL-EX-10)/alginic acid derivative (AL-EX-7-1-2) had a collapse rate of about 55% after 96 hours, suggesting improved stability in comparison with the alginic acid gel prepared from the alginic acid (ALG-2) for measuring gel stability (1).

<Measuring Gel Stability (3)>

A crosslinking group-introduced alginic acid derivative (AL-EX-2-1) with an introduction rate (NMR integration ratio) of 3.4 mmol % manufactured as in <Step 3> of (Example 2), the alginic acid derivative (AL-EX-8) obtained in Example 8, the alginic acid derivative (AL-EX-9) obtained in Example 9 and the alginic acid derivative (AL-EX-10) obtained in Example 10 were each dissolved to a concentration of 0.5% in water to obtain an aqueous alginic acid solution (2-1), aqueous alginic acid solution (8), aqueous alginic acid solution (9) and aqueous alginic acid solution (10). Three times the amount of phosphate buffered saline (PBS) was also added to a 2% crosslinking group-introduced alginic acid derivative (AL-EX-7-1-2) obtained by the methods of Example 7-1 (introduction rate (NMR integration ratio)=5.1 mol %) to obtain an aqueous alginic acid solution (7-1-2) with a concentration of 0.5%.

The aqueous alginic acid solution (2-1), aqueous alginic acid solution (8), aqueous alginic acid solution (9) and aqueous alginic acid solution (10) (250 µl) were each mixed with an equal amount of the aqueous alginic acid solution (7-1-2), and 40 ml of a 30 mmol/L calcium chloride solution was added to each mixture, which was then stirred for 5 minutes to obtain an alginic acid gel. 19.5 ml of 5 mM ethylenediamine tetraacetic acid dipotassium salt dihydrate (EDTA.2K)/physiological saline aqueous solution was added to each gel and shaken at 37° C., the aqueous solution was collected after 24 hours, and the gel was replenished with 5 mM EDTA.2K in the same amount as the collected amount. Upon completion of testing 10 µl of alginate lyase (Nippon Gene, 319-08261) was added to the test solution, which was then shaken overnight at 37° C. to completely collapse the gel, and the aqueous solution was collected. The alginic acid concentration in the collected aqueous solution was measured by the carbazole-sulfuric acid method, the alginic acid concentration in the aqueous solution at each point in time was corrected by the alginic acid concentration of the previously collected solution, the resulting value was divided by the total alginic acid concentration calculated from the alginic acid concentration at all time points and the alginic acid concentration after completion of testing, and the resulting value represented as a percentage was given as the gel collapse rate and used as an indicator of gel stability.

The results are shown in FIG. 4.

The crosslinked alginic acid structure obtained by crosslinking the alginic acid derivative (AL-EX-2-1)/alginic acid derivative (AL-EX-7-1-2) had a collapse rate of about 49% after 24 hours, the crosslinked alginic acid structure obtained by crosslinking the alginic acid derivative (AL-EX-9)/alginic acid derivative (AL-EX-7-1-2) had a collapse rate of about 28% after 24 hours, the crosslinked alginic acid structure obtained by crosslinking the alginic acid derivative (AL-EX-8)/alginic acid derivative (AL-EX-7-1-2) had a collapse rate of about 32% after 24 hours, and the crosslinked alginic acid structure obtained by crosslinking the alginic acid derivative (AL-EX-10)/alginic acid derivative (AL-EX-7-1-2) had a collapse rate of about 32% after 24 hours, confirming improved stability in all cases even with alginic acid structures from which the calcium crosslinking had been removed.

<Measuring Gel Leak Rate (1)>

The alginic acid derivative (AL-EX-2) obtained in <Step 3> of (Example 2), the alginic acid derivative (AL-EX-3) obtained in <Step 4> of (Example 3) or the raw material alginic acid without an introduced reactive group (ALG-2; control) was dissolved in water to a concentration of 1%, and 1/100 the amount of 1N-sodium hydrogen carbonate aqueous solution was added to obtain an aqueous alginic acid solution (2), aqueous alginic acid solution (3) and aqueous alginic acid solution (ALG-2-aq). An equal amount of fluorescein isothiocyanate-dextran (Sigma Aldrich, FD2000S) with a molecular weight of 2,000,000 prepared to 1 mg/ml with phosphate buffered saline (PBS) was also added to the 2 wt % alginic acid derivative (AL-EX-7-1) solution obtained in (Example 7-1) to obtain at 1 wt % aqueous alginic acid solution (7-1).

The aqueous alginic acid solution (2) or the aqueous alginic acid solution (3) was mixed with an equal amount of the aqueous alginic acid solution (7-1), and this mixed solution was placed in a syringe equipped with an 18-gauge needle, the syringe was attached to a syringe pump set to a flow rate of 1 ml/minute, and the solution was dripped for 30 seconds into a calcium chloride solution with a concentration of 30 mmol/L and stirred for 20 minutes to obtain an alginic acid gel. This gel was washed once with 10 ml of PBS to obtain a chemically crosslinked alginic acid gel containing fluorescein isothiocyanate-dextran. 20 ml of PBS was added to this gel and shaken at 37° C., and the aqueous solution was collected over time. Upon completion of testing, 5 µl of alginate lyase (Nippon Gene, 319-08261) was added to the test solution, which was then shaken for 2 hours at 37° C. to completely collapse the gel, and the aqueous solution was collected. The dextran concentration of the collected aqueous solution was measured by fluorescence assay (excitation light 485 nm, fluorescence 535 nm), and the dextran concentration at each point of time divided by the dextran concentration upon completion of testing expressed as a percentage was given as the leak rate and used as a measure of gel stability.

The results are shown in FIG. 2.

While the gel prepared from the alginic acid (ALG-2) used as a control exhibited a nearly 40% leak rate after 24 hours and a roughly 70% leak rate after 48 hours, the crosslinked alginic acid structures obtained by crosslinking the crosslinking group-introduced alginic acid derivatives of the examples (crosslinked alginic acid structure obtained by crosslinking alginic acid derivative (AL-EX-2)/alginic acid derivative (AL-EX-7-1) and crosslinked alginic acid structure obtained by crosslinking alginic acid derivative (AL-EX-3)/alginic acid derivative (AL-EX-7-1)) both had improved stability, with leak rates of about 10% after 24 hours and about 10% to 15% after 48 hours.

<Measuring Gel Permeability (2)>

A crosslinking group-introduced alginic acid derivative (AL-EX-2-1) with an introduction rate (NMR integration ratio) of 3.4 mmol % manufactured as in <Step 3> of (Example 2), the alginic acid derivative (AL-EX-8) obtained in Example 8, the alginic acid derivative (AL-EX-9) obtained in Example 9 and the alginic acid derivative (AL-EX-10) obtained in Example 10 were each dissolved in water to a concentration of 2.0% to prepare aqueous alginic acid solutions, 4/5 the amount of fluorescein isothiocyanate-dextran (Sigma Aldrich, FD150S) with a molecular weight of 150,000 adjusted to 1 mg/ml and 2.2 times the amount of water were added to each aqueous alginic acid solution, to obtain a 0.5% aqueous alginic acid solution (2-1), aqueous alginic acid solution (8), aqueous alginic acid solution (9) and aqueous alginic acid solution (10) each containing 0.2 mg/ml of fluorescein isothiocyanate-dextran. Three times the amount of phosphate buffered saline (PBS) was also added to a 2% crosslinking group-introduced alginic acid derivative (AL-EX-7-1-2) obtained by the methods of Example 7-1 (introduction rate (NMR integration ratio)=5.1 mol %) to obtain an aqueous alginic acid solution (7-1-2) with a concentration of 0.5%.

The aqueous alginic acid solution (2-1), aqueous alginic acid solution (8), aqueous alginic acid solution (9) and aqueous alginic acid solution (10) (250 µl) were each mixed with an equal amount of the aqueous alginic acid solution (7-1-1-2), and 40 ml of a 30 mmol/L calcium chloride solution was to each mixture, which was then stirred for 5 minutes to obtain an alginic acid gel. Each gel was washed once with 10 ml of physiological saline to obtain a chemically crosslinked alginic acid gel containing fluorescein isothiocyanate-dextran. 19.5 ml of physiological saline was added to each gel and shaken at 37° C., the aqueous solution was collected over time, and the gel was replenished with PBS in the same amount as the collected amount. Upon completion of testing 10 µl of alginate lyase (Nippon Gene, 319-08261) was added to the test solution, which was then shaken for 3 hours at 37° C. to completely collapse the gel, and the aqueous solution was collected. The dextran concentration in the collected aqueous solution was measured by fluorescence assay (excitation light 485 nm, fluorescence 535 nm), and the dextran concentration at each point of time divided by the dextran concentration upon completion of testing expressed as a percentage was given as the permeability.

The results are shown in FIG. 5.

The crosslinked alginic acid structure obtained by crosslinking the alginic acid derivative (AL-EX-2-1)/alginic acid derivative (AL-EX-7-1-2), the crosslinked alginic acid structure obtained by crosslinking the alginic acid derivative (AL-EX-9)/alginic acid derivative (AL-EX-7-1-2), the crosslinked alginic acid structure obtained by crosslinking the alginic acid derivative (AL-EX-8)/alginic acid derivative (AL-EX-7-1-2) and the crosslinked alginic acid structure obtained by crosslinking the alginic acid derivative (AL-EX-10)/alginic acid derivative (AL-EX-7-1-2) all exhibited nearly 20% leak rates after 3 hours and about 50% leak rates after 24 hours.

The invention claimed is:

1. An alginic acid derivative, ester thereof, or salt thereof which has at least one carboxyl group modified with a moiety represented by formula (II) below:

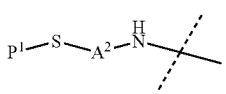
(II)

wherein $P^1$ is a hydrogen atom or a protecting group for a thiol group, and -$A^2$- is a linker represented by the following formula:

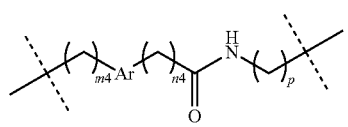

wherein Ar is a phenylene group optionally substituted with a water-soluble substituent;
n4 is an integer from 0 to 10;
m4 is an integer from 0 to 10; and
p is an integer from 0 to 10.

2. The alginic acid derivative, ester thereof, or salt thereof according to claim 1, wherein $P^1$ in formula (II) is a hydrogen atom, acetyl group or benzoyl group.

3. The alginic acid derivative, ester thereof, or salt thereof according to claim 1, wherein -$A^2$- is a linker selected from the group consisting of the following formulae:

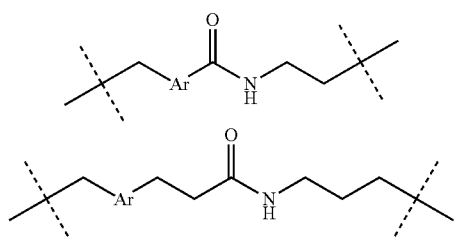

in which Ar is a p-phenylene group.

4. The alginic acid derivative, ester thereof, or salt thereof according to claim 1, wherein the group represented by formula (II) is selected from the group consisting of the following formulae:

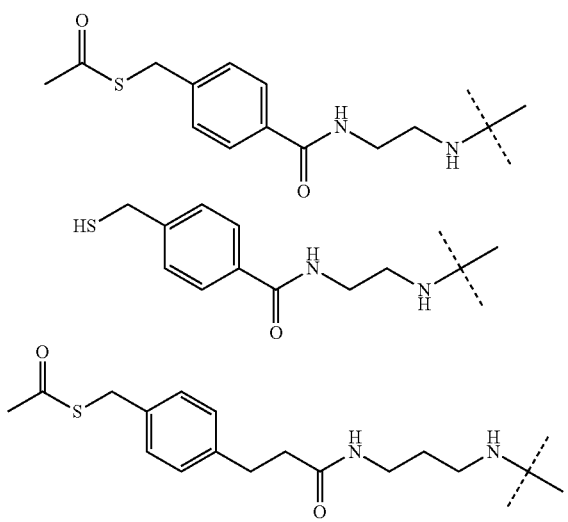

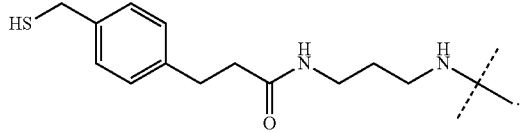

5. The alginic acid derivative, ester thereof, or salt thereof according to claim 1, wherein the group represented by formula (II) is selected from the group consisting of the following formulae:

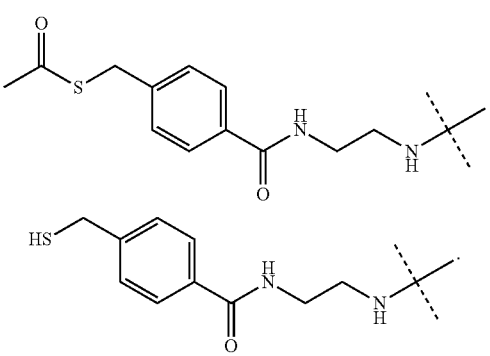

6. The alginic acid derivative, ester thereof, or salt thereof according to claim 1, wherein the introduction rate of the group represented by formula (II) is 1% to 30%.

7. The alginic acid derivative, ester thereof, or salt thereof according to claim 1 wherein the weight-average molecular weight as measured by gel filtration chromatography of the alginic acid derivative is 100,000 Da to 3,000,000 Da.

8. A composition comprising:
an alginic acid derivative, ester thereof, or salt thereof which has at least one carboxyl group which formed an amide bond with an amino group in a moiety represented by formula (I) below:

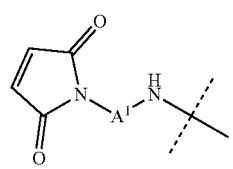
(I)

wherein -$A^1$- is a linker selected from the group consisting of the following formulae:

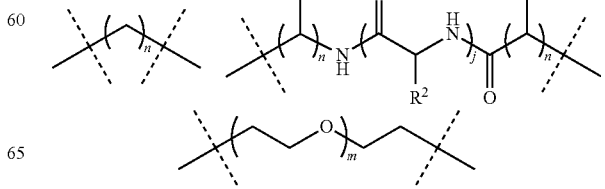

-continued

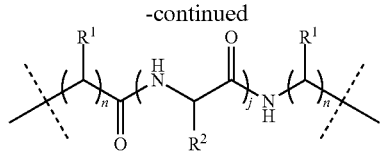

in which each $R^1$ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the $R^1$ binds and a nitrogen atom to which that carbon atom binds;

each $R^2$ is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the $R^2$ binds and a nitrogen atom to which that carbon atom binds;

n is an integer from 1 to 18;

m is an integer from 1 to 9; and j is an integer from 0 to 9; and an alginic acid derivative, ester thereof, or salt thereof according to claim 1.

9. A crosslinked alginic acid structure obtained by subjecting an alginic acid derivative, an ester thereof, or a salt thereof which has at least one carboxyl group which formed an amide bond with an amino group in a moiety represented by formula (I) below:

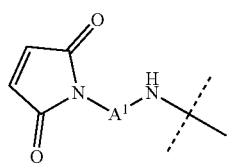 (I)

wherein -$A^1$- is a linker selected from the group consisting of the following formulae:

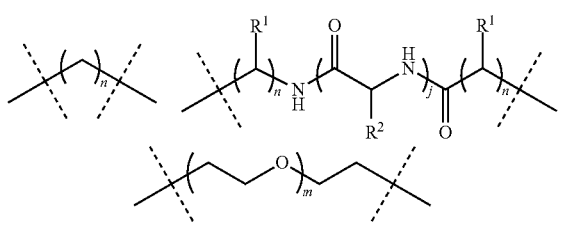

-continued

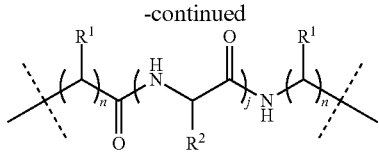

in which each $R^1$ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the $R^1$ binds and a nitrogen atom to which that carbon atom binds;

each $R^2$ is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the $R^2$ binds and a nitrogen atom to which that carbon atom binds;

n is an integer from 1 to 18;

m is an integer from 1 to 9; and j is an integer from 0 to 9, and an alginic acid derivative, ester thereof, or salt thereof according to claim 1 to a crosslinking reaction.

10. A medical material containing the crosslinked alginic acid structure according to claim 9.

11. The medical material according to claim 10, wherein the crosslinked alginic acid structure is a bead or a nearly spherical gel.

12. A method for manufacturing a crosslinked alginic acid structure, comprising:

dripping a solution of an alginic acid derivative, an ester thereof, or a salt thereof which has at least one carboxyl group which formed an amide bond with an amino group in a moiety represented by formula (I) below:

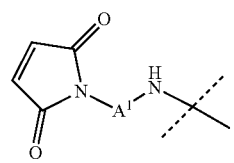 (I)

wherein -$A^1$- is a linker selected from the group consisting of the following formulae:

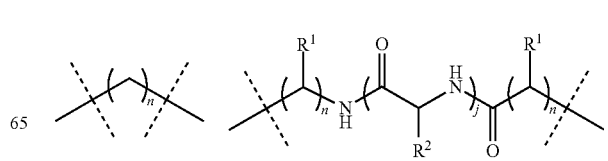

-continued

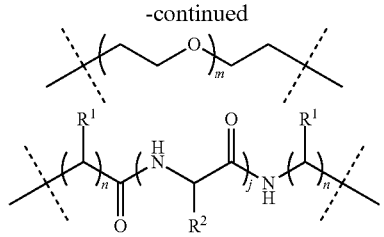

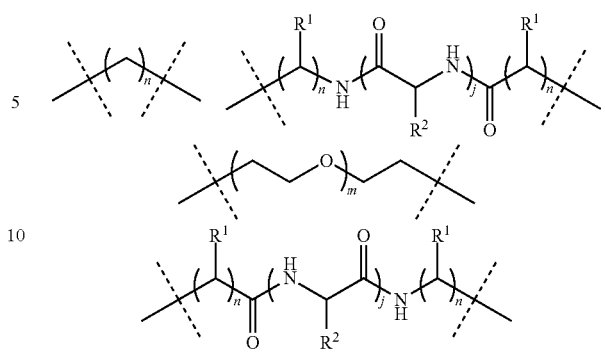

in which each $R^1$ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the $R^1$ binds and a nitrogen atom to which that carbon atom binds;

each $R^2$ is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the $R^2$ binds and a nitrogen atom to which that carbon atom binds;

n is an integer from 1 to 18;
m is an integer from 1 to 9; and
j is an integer from 0 to 9, into a solution containing a calcium ion to form a gel; and then subjecting the resulting gel to a crosslinking reaction in a solution of an alginic acid derivative, ester thereof, or salt thereof according to claim 1.

13. A method for manufacturing a crosslinked alginic acid structure, comprising:

dripping a solution of an alginic acid derivative, an ester thereof, or a salt thereof according to claim 1 into a solution containing a calcium ion; and then subjecting the resulting gel to a crosslinking reaction in a solution of an alginic acid derivative, an ester thereof, or a salt thereof which has at least one carboxyl group which formed an amide bond with an amino group in a moiety represented by formula (I) below:

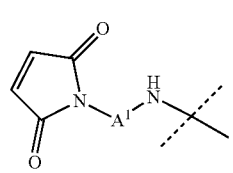

(I)

wherein -$A^1$- is a linker selected from the group consisting of the following formulae:

in which each $R^1$ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the $R^1$ binds and a nitrogen atom to which that carbon atom binds;

each $R^2$ is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the $R^2$ binds and a nitrogen atom to which that carbon atom binds;

n is an integer from 1 to 18;
m is an integer from 1 to 9; and
j is an integer from 0 to 9.

14. A method for manufacturing a crosslinked alginic acid structure, comprising:

dripping a solution of the composition according to claim 8 into a solution containing a calcium ion.

15. An alginic acid derivative, an ester thereof, or a salt thereof which has at least one carboxyl group which formed an amide bond with an amino group in a moiety represented by formula (I) below:

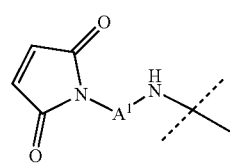

(I)

wherein -$A^1$- is a linker selected from the group consisting of the following formulae:

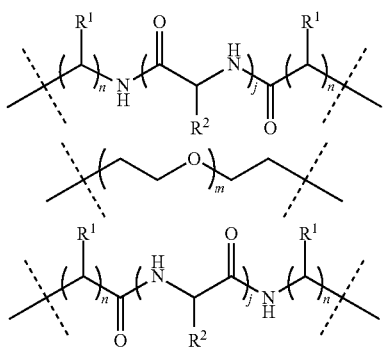

in which each R¹ independently represents a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the R¹ binds and a nitrogen atom to which that carbon atom binds;

each R² is independently a group selected from the group consisting of a hydrogen atom, methyl group, isopropyl group, isobutyl group, sec-butyl group, hydroxymethyl group, 2-hydroxyethyl group, thiolmethyl group, methylthioethyl group, carboxymethyl group, carboxyethyl group, aminocarbonylmethyl group, aminocarbonylethyl group, aminobutyl group, guanidinopropyl group, benzyl group, 4-hydroxybenzyl group, 3-indolylmethyl group, 4-imidazoylmethyl group, and a propane-1,3-diyl group that forms a ring together with a carbon atom to which the R² binds and a nitrogen atom to which that carbon atom binds;

n is an integer from 1 to 18;
m is an integer from 1 to 9; and
j is an integer from 0 to 9,
provided that —CH₂CH₂— as -A¹- is excluded.

16. The alginic acid derivative, ester or salt according to claim 15, wherein -A¹- is a linker selected from the group consisting of the following formulae:

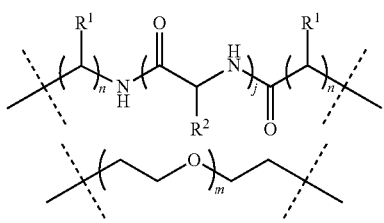

n is an integer from 1 to 18;
m is an integer from 1 to 9; and
j is an integer from 0 to 9.

17. The alginic acid derivative, ester or salt according to claim 15, wherein
-A¹- is a linker selected from the group consisting of the following formulae:

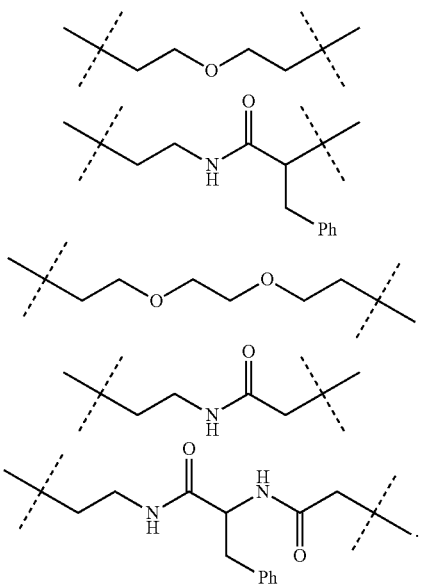

18. The alginic acid derivative, ester or salt according to claim 15, wherein the group represented by formula (I) is selected from the group consisting of the following formulae:

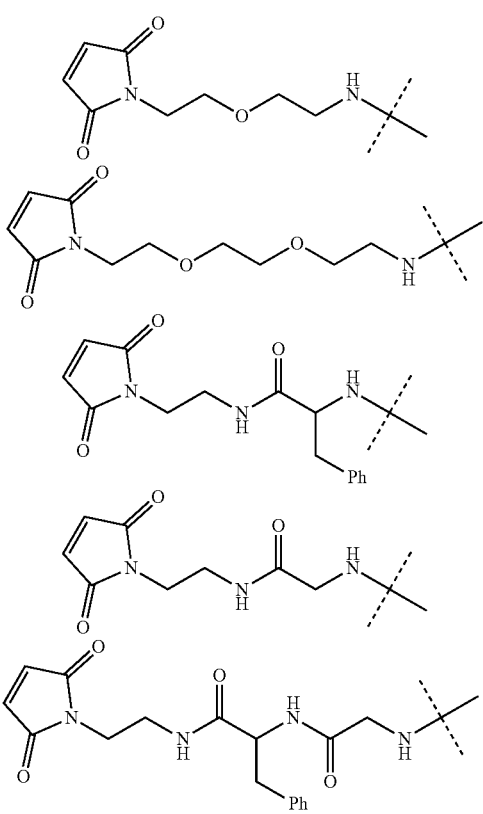

19. The alginic acid derivative, ester or salt according to claim 15, wherein the introduction rate of the group represented by formula (I) is 1% to 30%.

20. The alginic acid derivative, ester or salt according to claim 15, wherein the weight-average molecular weight as measured by gel filtration chromatography of the alginic acid derivative is 100,000 Da to 3,000,000 Da.

\* \* \* \* \*